United States Patent
Hubschwerlen et al.

(10) Patent No.: US 8,501,774 B2
(45) Date of Patent: *Aug. 6, 2013

(54) OXAZOLIDINONE-QUINOLONE HYBRID ANTIBIOTICS

(75) Inventors: Christian Hubschwerlen, Durmenach (FR); Jean-Luc Specklin, Kembs-Schaeferhof (FR); Daniel Baeschlin, Arlesheim (CH); Christine Schmitt, Kunheim (FR); Stefan Muller, Oberentfelden (CH); Michael W. Cappi, München (DE)

(73) Assignee: Morphochem Aktiengesellschaft für Kombinatorische Chemie, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/368,667

(22) Filed: Feb. 8, 2012

(65) Prior Publication Data

US 2012/0142635 A1  Jun. 7, 2012

Related U.S. Application Data

(63) Continuation of application No. 10/583,419, filed as application No. PCT/EP2004/014500 on Dec. 20, 2004, now Pat. No. 8,158,797.

(60) Provisional application No. 60/530,822, filed on Dec. 18, 2003.

(30) Foreign Application Priority Data

Jan. 23, 2004  (EP) .................................. 04 001 506

(51) Int. Cl.
*A61K 31/47*  (2006.01)
*C07D 471/04*  (2006.01)

(52) U.S. Cl.
USPC ........... 514/314; 514/290; 514/319; 514/320; 514/321; 546/123; 546/134; 546/156

(58) Field of Classification Search
USPC .................. 546/123, 156, 134; 514/290, 319, 514/320, 321, 314
See application file for complete search history.

(56) References Cited

U.S. PATENT DOCUMENTS

| | | |
|---|---|---|
| 4,840,956 A | 6/1989 | Domagala et al. |
| 5,221,676 A | 6/1993 | Laborde et al. |
| 5,491,139 A | 2/1996 | Demuth, Jr. et al. |
| 5,599,791 A | 2/1997 | Tavecchia et al. |
| 5,808,076 A | 9/1998 | Vetter et al. |
| 5,861,413 A | 1/1999 | Habich et al. |
| 5,998,436 A | 12/1999 | Yazaki et al. |
| 6,239,152 B1 | 5/2001 | Gordeev et al. |
| 2004/0132764 A1 | 7/2004 | Locher |

FOREIGN PATENT DOCUMENTS

| | | |
|---|---|---|
| DE | 196 01 265 A1 | 7/1997 |
| EP | 0 266 576 A2 | 5/1988 |
| EP | 0 390 215 A2 | 10/1990 |
| HU | 224 072 B1 | 5/2005 |
| JP | 02069478 A | 3/1990 |
| JP | 2000-516239 T | 12/2000 |
| KR | 10 2000 0067306 | 11/2000 |
| KR | 2004-30712 Y1 | 11/2006 |
| RU | 2167873 C2 | 5/2001 |
| WO | 93/09103 A1 | 5/1993 |
| WO | 97/30995 A1 | 8/1997 |
| WO | 99/28317 A1 | 6/1999 |
| WO | 00/10566 A1 | 3/2000 |
| WO | 01/09107 A1 | 2/2001 |
| WO | 01/46164 A1 | 6/2001 |
| WO | 02/059116 A | 8/2002 |
| WO | 03/002560 A | 1/2003 |
| WO | 03/031441 A1 | 4/2003 |
| WO | 03/031443 A | 4/2003 |
| WO | 03/031443 A1 | 4/2003 |
| WO | 03/032962 A | 4/2003 |
| WO | 2004/069816 A1 | 8/2004 |
| WO | 2004/096221 A1 | 11/2004 |
| WO | 2005/023801 A1 | 3/2005 |
| WO | 2007017828 A2 | 2/2007 |
| WO | 2008056335 A1 | 5/2008 |
| WO | 2008062379 A2 | 5/2008 |
| WO | 2009136379 A1 | 11/2009 |

*Primary Examiner* — Rita Desai
(74) *Attorney, Agent, or Firm* — Edwards Wildman Palmer LLP; Peter F. Corless; Christine C. O'Day

(57) ABSTRACT

The present invention relates to compounds of the Formula (I) that are useful antimicrobial agents and effective against a variety of multi-drug resistant bacteria:

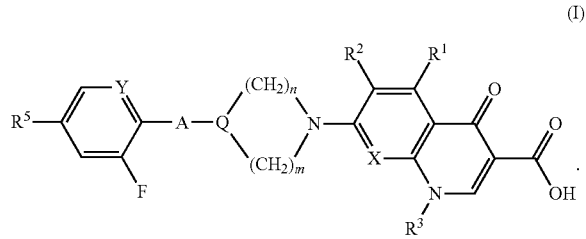

10 Claims, No Drawings

OXAZOLIDINONE-QUINOLONE HYBRID ANTIBIOTICS

RELATED APPLICATIONS

This application is a continuation of U.S. Ser. No. 10/583,419, filed on Jun. 16, 2006 (371(c) date of Sep. 28, 2007), which is a US National stage application of PCT/EP2004/014500 (WO2005/058888), filed on Dec. 20, 2004, which claims priority to U.S. Ser. No. 60/530,822, filed on Dec. 18, 2003, and EP04001506.7, filed on Jan. 23, 2004. The entire contents of the above-referenced applications are incorporated herein by reference.

The present invention describes new compounds in which the pharmacophores of quinolone and oxazolidinone are linked together through a linker that is stable under physiological conditions and a pharmaceutical antibacterial composition containing these compounds. These dual action compounds are useful antimicrobial agents effective against a variety of human and veterinary pathogens including Gram positive aerobic bacteria such as multiply-resistant staphylococci, streptococci and enterococci as well as Gram negative bacteria such as *Moraxella catarrhalis* and *Haemophilus influenzae* and anaerobic organisms such as *bacteroides* spp. and *Clostridia* spp. species and acid-fast organism such as *Mycobacterium tuberculosis, Mycobacterium avium* spp.

Oxazolidinone-quinolone hybrid antibiotics have already been described (WO02059116, WO03002560, WO03031443, WO03032962). The major drawback of the compounds known in the state of the art is the poor water solubility, which makes the development of a formulation difficult.

The present invention provides new compounds of formula (I), that are useful antimicrobial agents and effective against a variety of multi-drug resistant bacteria

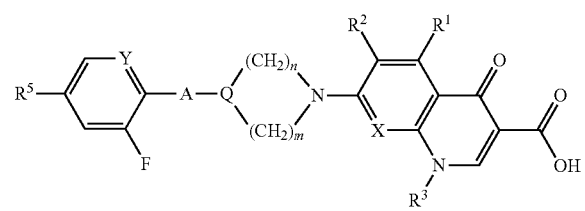

(I)

wherein
A is an alkylene group, an alkenylene group, an alkynylene group, a heteroalkylene group, a cycloalkylene group, a heterocycloalkylene group, an arylene group or a heteroarylene group all of which groups may be substituted;
Q is $CR^4$ or N (especially $CR^4$);
X is $CR^7$ or N;
Y is $CR^6$ or N;
n is 1, 2 or 3;
m is 1, 2 or 3;
$R^1$ is H, F, Cl, Br, I, OH, $NH_2$, an alkyl group or a heteroalkyl group;
$R^2$ is H, F or Cl;
$R^3$ is H, an alkyl group, an alkenyl group, an alkynyl group, a heteroalkyl group, a cycloalkyl group, a heterocycloalkyl group, an aryl group, a heteroaryl group, an alkylaryl group or a heteroarylalkyl group; all of which groups may be substituted with one, two or more halogen atoms like F or Cl or amino groups.
$R^4$ is hydroxy, a group of formula $OPO_3R^9{}_2$ or $OSO_3R^{10}$ or a heteroalkyl group carrying at least one OH, $NH_2$, $SO_3R^{10}$, $PO_3R^9{}_2$ or COOH group or an ester of a naturally occurring amino acid or a derivative thereof, wherein the groups $R^9$ independently of each other are H, alkyl, cycloalkyl, aryl or aralkyl and wherein $R^{10}$ is H, alkyl, cycloalkyl, aryl or aralkyl;
$R^5$ is selected from following groups:

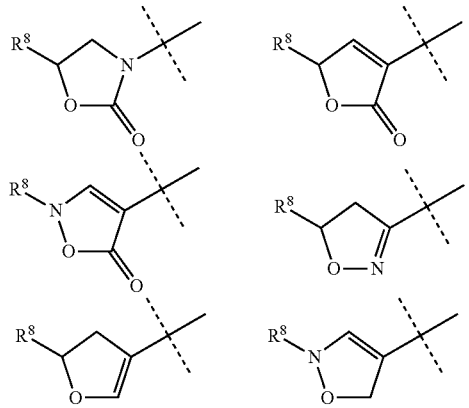

$R^6$ is H, F, Cl or OMe;
$R^7$ is H, F, Cl, OH, $NH_2$, a substituted or unsubstituted alkyl group or a substituted or unsubstituted hetero-alkyl group, or
$R^3$ and $R^7$ can be linked via an alkylene, an alkenylene or a heteroalkylene group or be a part of a cycloalkylene or heterocycloalkylene group; in case $R^3$ is no H and $R^7$ is no H, F, OH, $NH_2$ or Cl; and
$R^8$ is a $C_{1-6}$ heteroalkyl, a heteroarylalkyl, a hetero-alkylaryl or a heteroalkylheteroaryl group;
or a pharmacologically acceptable salt, solvate, hydrate or formulation thereof.

It should be appreciated that certain compounds of formula (I) or (II) as mentioned in this description may have tautomeric forms from which only one might be specifically mentioned or depicted in this description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). Further, some compounds may display polymorphism. All these tautomeric forms, geometrical or optical isomers (as well as racemates and diastereomers) and polymorphous forms are included in the invention.

The term alkyl refers to a saturated straight or branched chain alkyl group, preferably containing from one to ten, preferably one to six carbon atoms, for example methyl, ethyl, propyl, isopropyl, butyl, iso-butyl, sec-butyl, tert-butyl, n-pentyl, iso-pentyl, n-hexyl, 2,2-dimethylbutyl, n-octyl or n-pentyl groups. Any alkyl group as defined herein may be substituted with one, two or more substituents, for example F, Cl, Br, I, $NH_2$, OH, SH or $NO_2$.

The terms alkenyl and alkynyl refer to an unsaturated straight or branched chain alkyl group (having one, two or more double and/or triple bonds, an alkenyl preferably having one or two double bonds and an alkynyl preferably having one or two triple bonds), preferably containing two to ten, preferably two to six carbon atoms for example: ethenyl (vinyl), propenyl (allyl), iso-propenyl, n-pentenyl, butenyl, isoprenyl or hexa-2-enyl; ethynyl, propynyl or butynyl groups. Any alkenyl or alkynyl group as defined herein may be substituted with one, two or more substituents, for example F, Cl, Br, I, $NH_2$, OH, SH or $NO_2$.

The term heteroalkyl refers to an alkyl, alkenyl or alkynyl group as defined herein where one or more carbon atoms are replaced by an oxygen, nitrogen, phosphorous or sulphur atom, for example an alkoxy group such as methoxy, ethoxy, propoxy, iso-propoxy, butoxy or tert.-butoxy, an alkoxyalkyl group such as methoxymethyl, ethoxymethyl, 1-methoxy-ethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. It may also refer to one of the above groups containing a keto group. The term heteroalkyl furthermore refers to a group derived from a carboxylic acid or carboxylic acid amide such as acetyl, propionyl, acetyloxy, propionyloxy, acetylamino or propionylamino, a carboxyalkyl group such as carboxymethyl, carboxyethyl or carboxypropyl, a carboxyalkyl ester, an alkylthiocarboxyamino group, an alkoxyimino group, an alkylaminothiocarboxyamino group or an alkoxycarbonylamino group. Any heteroalkyl group as defined herein may be substituted with one, two or more substituents, for example F, Cl, Br, I, $NH_2$, OH, SH or $NO_2$.

The term cycloalkyl refers to a saturated or partially unsaturated (having one, two or more double and/or triple bonds) cyclic group with one, two or more rings, having three to 14 carbon ring-atoms, preferably from five or six to ten carbon ring-atoms, for example cyclopropyl, cyclobutyl, cyclopentyl, cyclohexyl, tetralin, cyclopentenyl or cyclohex-2-enyl groups. Any cycloalkyl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide.

The term heterocycloalkyl refers to a cycloalkyl group as defined herein where one, two or more carbon ring-atoms are replaced by one, two or more oxygen, nitrogen, phosphorous or sulphur atoms or $S(O)_{1-2}$ groups for example piperidino, morpholino or piperazino groups.

The term aryl refers to an aromatic cyclic group with one, two or more rings, having five to 14 carbon ring-atoms preferably from five or six to ten carbon ring-atoms, for example phenyl or naphthyl groups. Any aryl group as defined herein may be substituted with one, two or more substituents, for example F, Cl, Br, I, OH, $NH_2$, SH, $NO_2$, alkyl groups such as methyl or ethyl, heteroalkyl groups such as methoxy, methylamino, dimethylamino or cyanide.

The term heteroaryl refers to an aryl group as defined herein where one, two or more ring-carbon atoms are replaced by an oxygen, nitrogen, boron, phosphorous or sulphur atom, for example pyridyl, imidazolyl, pyrazolyl, quinolinyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl and pyridazinyl groups.

The term aralkyl (or arylalkyl or alkylaryl) refers to groups that comprise both aryl as well as alkyl and/or cycloalkyl groups.

The term heteroarylalkyl (or heteroalkylaryl or heteroalkylheteroaryl etc.) refers to an aralkyl group as defined herein where one, two, three or more carbon atoms are replaced by one, two, three or more oxygen, nitrogen, phosphorous or sulphur atoms or $S(O)_{1-2}$ groups.

Any alkyl, alkenyl, alkynyl, heteroalkyl, cycloalkyl, heterocycloalkyl, aryl, heteroaryl, aralkyl or heteroaryl-alkyl groups as defined herein may be substituted with one or more halogen atoms, $NH_2$, SH, $NO_2$ or OH groups or unsubstituted alkyl, heteroalkyl, aryl, aralkyl, aralkyl-oxy, heteroaryl, cycloalkyl or heterocycloalkyl groups as defined herein.

The term "optionally substituted" or "substituted" refer to groups wherein one or more hydrogen atoms may be replaced by a halogen atom, a $NH_2$, SH, $NO_2$ or OH group or by an unsubstituted alkyl, heteroalkyl, aryl, aralkyl, aralkyloxy, heteroaryl, cycloalkyl or heterocycloalkyl group as defined herein.

Preferred and/or advantageous embodiments of the invention are subject-matter of the subclaims.

Preferred are compounds of Formula (I), wherein $R^1$ is H.

Further preferred are compounds of Formula (I), wherein $R^2$ is F or H.

Moreover preferred are compounds of Formula (I), wherein $R^3$ is an ethyl, a 2-propyl, a $C_3$-$C_6$ cycloalkyl (i.e. cyclopropyl, cyclobutyl, cyclopentyl or cyclohexyl), a phenyl or a pyridyl group. All these groups may be substituted with one, two, three or more fluorine atoms or amino groups.

Moreover preferred are compounds of Formula (I), wherein $R^3$ is a cyclopropyl group.

Further preferred are compounds of Formula (I), wherein $R^7$ and $R^3$ together form a bridge of the formula —O—$CH_2$—N(Me)- or —O—$CH_2$—CH(Me)-. Herein, the preferred stereochemistry at the chiral center is the one giving the (S) configuration in the final compound.

Moreover preferred are compounds of formula (I), wherein $R^4$ is hydroxy or a group of formula $OSO_3H$, $OPO_3H_2$, $OCH_2OPO_3H_2$, $OCOCH_2CH_2COOH$ or an ester of a naturally occurring amino acid or a derivative thereof (i.e. a group of formula —OCOCHR'$NH_2$ or a derivative like an ester, amide or alkylamine thereof, wherein R' is the side chain of a naturally occurring amino acid like aspartic acid, glutaric acid, lysine, etc; e.g. dimethyl aminoglycine $OCOCH_2N(CH_3)_2$).

Further preferred are compounds of Formula (I), wherein $R^8$ is a group of the formula —$CH_2$NHCOCH=CHAryl, —$CH_2$OHeteroaryl (especially -oxa-3-oxazol), —$CH_2$NHSO$_2$Me, —$CH_2$NHCOOMe, —$CH_2$NHCOMe, —$CH_2$NHCS$_2$Me, —$CH_2$NHCSMe, —$CH_2$NHCSNH$_2$, —$CH_2$NHCSOMe or —NHCOMe; especially —$CH_2$NHCSMe or —$CH_2$NHCOMe.

Especially preferred are compounds of Formula (I), wherein $R^5$ has the following structure:

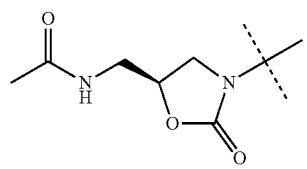

Moreover preferred are compounds of Formula (I), wherein $R^7$ is H, F, Cl or a methoxy group that may be substituted by one, two or three fluorine atoms.

Further preferred are compounds of formula (I), wherein X is N or CH.

Moreover preferred are compounds of Formula (I), wherein Y is CH or N.

Further preferred are compounds of Formula (I), wherein A is $C_{1-6}$ alkylene, $C_{2-6}$ alkenylene, $C_{2-6}$ alkynylene, $C_{1-6}$ heteroalkylene, cyclopropylene, epoxide, aziridine, thioepoxide, lactame or lactone, all of which groups may be substituted.

Moreover preferred are compounds of formula (I), wherein A is a group of Formula —O—B—, wherein B is a $C_{1-4}$ alkylene group, a $C_{2-4}$ alkenylene group, a $C_{2-4}$ alkynylene group or a $C_{1-4}$ heteroalkylene group, all of which groups may be substituted by one, two or more hydroxy or amino groups.

Especially preferred are compounds of formula (I), wherein A is a group of formula —$CH_2CH_2$—, —$OCH_2$—, —$OCH_2CH_2$—, —$SCH_2$—, —$SCH_2CH_2$—, —CH=CH—, —C≡C—, —CH(OH)CH(OH)— or —CH($NH_2$)CH(OH)—.

Especially preferred are compounds of formula (I), wherein B is $CH_2$ or $CH_2CH_2$.

Especially preferred are compounds of formula (II)

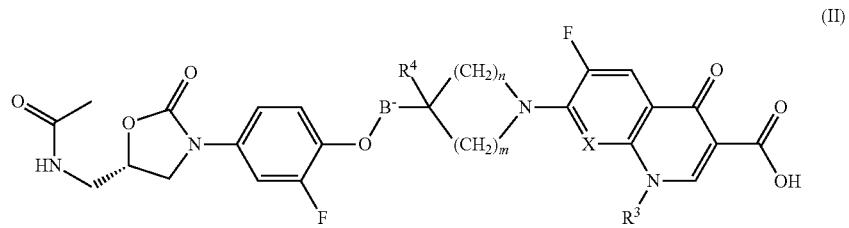

(II)

wherein the residues are defined as above. In a preferred embodiment B is $CH_2$ or $CH_2CH_2$; X is CH, N or C—OMe and $R^3$ is cyclopropyl or X is $CR^7$ and $R^7$ and $R^3$ together form a bridge of the formula —O—$CH_2$—CH(Me)-, wherein the preferred stereochemistry at the chiral center is the one giving the (S) configuration in the final compound, n is 1, 2 or 3, m is 1, 2 or 3 and $R^4$ is hydroxy or a group of formula $OSO_3H$, $OPO_3H_2$, $OCH_2OPO_3H_2$, $OCOCH_2CH_2COOH$ or an ester of a naturally occurring amino acid or a derivative thereof.

Moreover preferred are the mono, di or tri sodium salts (most preferred the mono sodium salts) of compounds of formula (I) or (II) or mixtures thereof. Especially preferred are the mono, di or tri sodium salts (most preferred the mono sodium salts) of compounds of formula (I) or (II), wherein $R^4$ is $OPO_3H_2$ or $OSO_3H$ or mixtures thereof.

Especially preferred is the sodium salt of a compound of formula (II) wherein $R^3$ is a cyclopropyl group, X is CH or N, n is 2, m is 2, $R^4$ is $OPO_3H_2$ and B is $CH_2$.

The present invention also relates to pharmacologically acceptable salts, or solvates and hydrates, respectively, and to compositions and formulations of compounds of Formula (I) or (II). The present invention describes procedures to produce pharmaceutically useful agents, which contain these compounds, as well as the use of these compounds for the production of pharmaceutically useful agents.

The pharmaceutical compositions according to the present invention contain at least one compound of Formula (I) or (II) as the active agent and optionally carriers and/or diluents and/or adjuvants. Optionally the pharmaceutical compositions according to the present invention may also contain additional known antibiotics.

Examples of pharmacologically acceptable salts of sufficiently basic compounds of Formula (I) or (II) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of Formula (I) or (II) may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts. Compounds of Formula (I) or (II) may be solvated, especially hydrated. The hydratisation can occur during the process of production or as a consequence of the hygroscopic nature of the initially water free compounds of Formula (I) or (II). The compounds of Formula (I) or (II) may contain asymmetric C-atoms and may be present either as achiral compounds, mixtures of diastereomers, mixtures of enantiomers or as optically pure compounds.

The present invention also relates to pro-drugs which are composed of a compound of Formula (I) or (II) and at least one pharmacologically acceptable protective group which will be cleaved off under physiological conditions, such as an alkoxy-, aralkyloxy-, acyl-, $SO_3H$, $PO_3H_2$, acyloxymethyl group (e.g. pivaloyloxymethyl), an 2-alkyl-, 2-aryl- or 2-aralkyl-oxycarbonyl-2-alkylidene ethyl group or an acyloxy group as defined herein, e.g. ethoxy, benzyloxy, acetyl or acetyloxy. Especially preferred are prodrugs of the hydroxy group of a compound of formula (I) or (II) wherein $R^4$ is OH.

As mentioned above, therapeutically useful agents that contain compounds of Formula (I) or (II), their solvates, salts or formulations are also comprised in the scope of the present invention. In general, compounds of Formula (I) or (II) will be administered by using the known and acceptable modes known in the art, either alone or in combination with any other therapeutic agent. Such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatin, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilisation, e.g. UV stabilizers, emulsifiers, sweetener, aromatisers, salts to change the osmotic pressure, buffers, coating additives and antioxidants.

A daily dosage per patient of about 1 mg to about 4000 mg especially about 50 mg to 3 g is usual with those of ordinary skill in the art appreciating that the dosage will depend also upon the age, conditions of the mammals, and the kind of diseases being treated or prevented. The daily dosage can be administrated in a single dose or can be divided over several doses. An average single dose of about 50 mg, 100 mg, 250 mg, 500 mg, 1000 mg and 2000 mg can be contemplated.

The compounds of formula (I) and (II) can be synthesized according to the following reaction scheme:

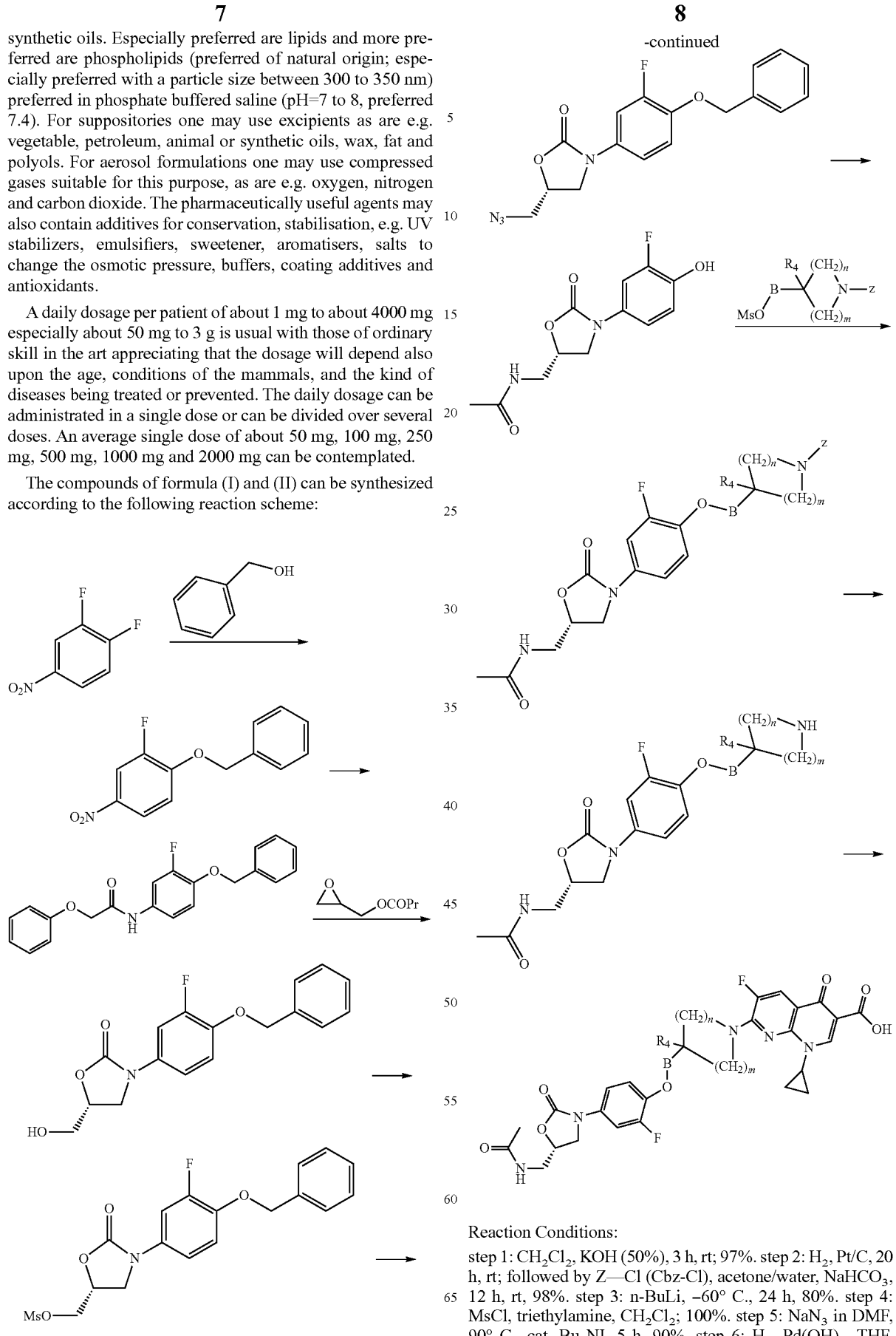

Reaction Conditions:

step 1: $CH_2Cl_2$, KOH (50%), 3 h, rt; 97%. step 2: $H_2$, Pt/C, 20 h, rt; followed by Z—Cl (Cbz-Cl), acetone/water, $NaHCO_3$, 12 h, rt, 98%. step 3: n-BuLi, −60° C., 24 h, 80%. step 4: MsCl, triethylamine, $CH_2Cl_2$; 100%. step 5: $NaN_3$ in DMF, 90° C., cat. $Bu_4NI$, 5 h, 90%. step 6: $H_2$, $Pd(OH)_2$, THF, MeOH, 24 h, followed by AcOH, Ac₂O, rt, 2 h, 70%. step 7: DMF, NaH, 70° C., 12 h, 75%. step 8: H₂, Pd(OH)₂, MeOH, THF, 24 h, RT, 100%. step 9: N-Methylpyrrolidinone, 1-Cyclopropyl-7-chloro-6-fluoro-1,4-dihydro-4-oxo-1,8-naphthydrin-3-carboxylic acid (commercially available), TMS-Cl, Hünig Base or K₂CO₃, 80° C., 5 h, 80%.

EXAMPLES

Example 1

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-[1,8]naphthyridine-3-carboxylic Acid

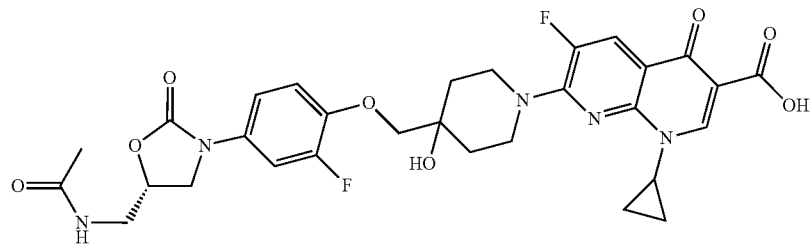 [SMILES: CC(=O)NC[C@H]1CN(c2ccc(OCC3(O)CCN(c4nc5c(cc4F)c(=O)c(C(=O)O)cn5C4CC4)CC3)c(F)c2)C(=O)O1]

Step 1: (4-Benzyloxy-3-fluoro-phenyl)-carbamic acid benzyl ester

A solution of 34.9 g 1-benzyloxy-2-fluoro-4-nitro-benzene (WO03064413) (MW: 247.28, 141 mmol) and 340 mg platinium 5% on activated carbon in 350 ml ethyl acetate was stirred under hydrogen at rt and normal pressure. The reaction was monitored by HPLC and was complete after twenty hours. The catalyst was filtered over a glass fiber filter, and the filtrate evaporated under reduced pressure to dryness. The oily residue was dissolved in 500 ml acetone and treated with 250 ml of a saturated solution of sodium bicarbonate and 17.5 g of sodium bicarbonate (MW: 84.01, 208 mmol). The mixture was cooled to 5° C. and treated drop wise with 26.08 g of benzyl chloroformate (MW: 170.59, 152 mmol). The reaction was allowed to stirred at room temperature for two hours and monitored by TLC (hexane/ethyl acetate 3:1). The acetone was evaporated, the residue diluted with 500 ml water, and the solid filtered off. The crystals were washed with 500 ml water and dried. Yield: 48.05 g, 95.8%. MS: 352.5 (M+H)⁺, 350.8, (M−H)⁻. Method ESI⁺, ESI⁻.

Step 2: (5R)-3-(4-benzyloxy-3-fluoro-phenyl)-5-hydroxy-methyl-oxazolidin-2-one

A stirred solution of 17.5 g (4-benzyloxy-3-fluoro-phenyl)-carbamic acid benzyl ester (MW: 351.38, 50 mmol) in 30 ml of dry tetrahydrofuran was cooled to −78° C. with a dry ice/acetone bath. 22.8 ml of a 2.3M n-butyl-lithium solution in n-hexane (52.5 mmol) was added drop wise and the reaction mixture stirred at −78° C. for 15 min. 7.92 g R(−)-glycidyl butyrate (MW: 144.17, 60 mmol) were added and the reaction was allowed to warm up to room temperature. The reaction was monitored by HPLC, quenched with a saturated ammonium chloride solution and diluted with 100 ml of ethyl acetate. The organic layer was washed with 200 ml water and 200 ml brine. The organic layer was dried over magnesium sulfate, filtered and the filtrate evaporated under reduced pressure. The residue was crystallized from 200 ml of a 1/1-ethyl acetate/hexane mixture. The solid was collected and recrystallized from 150 ml of a 9/1 ethyl acetate/dichloro-methane mixture. The colorless crystals were collected and dried. Yield: 10.4-g, 65.5%. MS: 318.1 (M+H)⁺. Method ESI⁺.

Step 3: (5S)-5-azidomethyl-3-(4-benzyloxy-3-fluoro-phenyl)-oxazolidin-2-one

A solution of 10 g (5R)-3-(4-benzyloxy-3-fluoro-phenyl)-5-hydroxymethyl-oxazolidin-2-one (MW: 317.32, 31.51 mmol) and 4.78 g triethylamine (MW: 101.19, 47.26 mmol) in 300 ml dichloromethane was treated under stirring at 10° C. with 4.32 g of methane sulfonyl chloride (MW: 114.55, 37.82 mmol). The reaction was stirred at room temperature for one hour and monitored by TLC (ethyl acetate: hexane 1:1). The reaction mixture was quenched with 100 ml water and the organic layer washed with 100 ml brine. The organic layer was dried over magnesium sulfate, filtered and the filtrate evaporated under reduced pressure. The residue was dissolved in 100 ml dimethylformamide, 5.12 g sodium azide (MW: 65.01, 78.7 mmol) and a catalytic amount of tetrabutyl ammonium iodide were added. The suspension was stirred at 90° C. over night. The reaction was monitored by HPLC. The dimethylformamide was evaporated under reduced pressure, the residue dissolved in 200 ml dichloromethane and the organic layer washed successively with 100 ml water and 100 ml brine. The dichloromethane solution was dried over magnesium sulfate, filtered, and the filtrate evaporated under reduced pressure. The residue was crystallized from 150 ml of a 1/1 mixture of ethyl acetate: hexane. The crystals were collected to afford an off white solid. Yield: 10.4-g, 97%. MS: 343.1 (M+H)⁺⁻. Method: ESI⁺.

Step 4: N-[(5S)-{3-(3-fluoro-4-hydroxy-phenyl)}-2-oxo-oxazolidin-5-ylmethyl]-acetamide A suspension of 10.4 g (5S)-5-azidomethyl-3-(4-benzyloxy-3-fluorophenyl)oxazolidin-2-one (MW: 342.33, 30.38 mmol) and 1.5 g of palladium 10% on activated carbon in 400 ml of a 1:1 methanol:ethyl acetate mixture was stirred at room temperature under hydrogen for two days. The catalyst was filtered off using a glass fibre filter paper and the filtrate evaporated under reduced pressure. The residue was dissolved in 100 ml of acetic acid, and treated with 3.72 g of acetic anhydride (MW: 102.09, 36.45 mmol). The solvent was evaporated under reduced pressure and the residue crystallized from a 1:1 ethyl acetate: hexane mixture to afford an off white solid. Yield: 6.76-g, 83%. MS: 269.4 (M+H)⁺, 267.3, (M−H)⁻. Method ESI⁺, ESI⁻.

Step 5: 4-{4-[(5S)-5-(Acetylamino-methyl)-2-oxo-oxazolidin-3-yl]-2-fluoro-phenoxymethyl}-4-hydroxy-piperidine-1-carboxylic Acid Benzylester A suspension of 22.72 g 1-oxa-6-aza-spiro[2.5]octane-6-carboxylic acid benzyl ester (WO9803507) (MW: 247.29, 92 mmol), 21.45 g N-[(5S)-{3-(3-fluoro-4-hydroxy-phenyl)}-2-oxo-oxazolidin-5-ylmethyl]-acetamide (MW: 268.246, 80 mmol) and 16.58 g potassium carbonate (MW: 138.20, 120 mmol) in 150 ml dimethylformamide was stirred at 100° C. for 7 hours. The reaction was monitored by TLC (dichloromethane/methanol 9:1). The dimethylformamide was evaporated under reduced pressure and the residue was dissolved in 600 ml of a 9:1 dichloromethane/methanol mixture. The organic layer was washed with 400 ml water and 400 ml brine. The organic layer was dried over magnesium sulfate, filtered, and the filtrate diluted with 250 ml ethyl acetate. The mixture was concentrated under reduced pressure to a final volume of 400 ml. The slurry was stirred at room temperature over night. The crystals were filtered and washed successively with 150 ml ethyl acetate and 100 ml pentane. Yield: 31.65 g, 76.7%. MS: 516.8 (M+H)+, Method ESI+.

Step 6: N-[{(5S)-3[3-fluoro-4-(4-hydroxy-piperidin-4-yl-methoxy)-phenyl]-2-oxo-oxazolidin-5-ylmethyl}]-acetamide A suspension of 31 g 4-{4-[(5S)-5-(acetylamino-methyl)-2-oxo-oxazolidin-3-yl]-2-fluorophenoxymethyl}-4-hydroxy-piperidine-1-carboxylic acid benzylester (MW: 515.54 60.13 mmol) and 2.5 g of palladium 10% on activated carbon in 310 ml methanol and 150 ml ethyl acetate was stirred under hydrogen for 4 hrs. The reaction was monitored by TLC (ethyl acetate). The reaction slurry was diluted with 300 ml methanol, warmed to 40° C., and the catalyst filtered off using a glass fibre filter paper. The filtrate was concentrated to 150 ml, diluted with 300 ml ethyl acetate and concentrated again to 200 ml. 200 ml of diethyl ether were added, and the suspension was cooled to 0° C. under stirring. The solid was collected and dried. Yield: 21.6-g, 94.3%. MS: 382.6 (M+H)+, Method ESI+.

Step 7: 7-(4-{[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-[1,8]naphthyridine-3-carboxylic acid A suspension of 71 mg 7-chloro-1-cyclopropyl-6-fluoro-1,4-dihydro-4-oxo-[1,8]naphthyridine-3-carboxylic acid (MW: 282.66, 0.25 mmol), 95 mg N-[{(5S)-3[3-fluoro-4-(4-hydroxy-piperidin-4-ylmethoxy)-phenyl]-2-oxo-oxazolidin-5-ylmethyl}]-acetamide (MW: 381.40, 0.25 mmol) 102 mg triethylamine (MW: 101.19, 1.0 mmol) and 81 mg trimethylchlorsilan (MW: 108.64, 0.75 mmol) in 1 ml N-methyl-pyrrolidin-2-one was heated at 80° C. under stirring for 5 hours. The reaction was monitored by TLC (dichloromethane:methanol 9:1). The N-methyl-pyrrolidin-2-one was evaporated, the residue dissolved in 20 ml of a 9:1 dichloromethane:methanol mixture, and the solution washed sequentially with 10 ml of 0.1 N aqueous hydrochloric acid and 20 ml brine. The organic layer was dried over magnesium sulfate, filtered and the filtrate evaporated. The residue was dissolved in 10 ml of a 9:1 dichloromethane: methanol mixture and diluted with 20 ml ethyl acetate. The precipitated solid was collected to afford an off white solid. A second crop is obtained by concentration under reduced pressure of the mother liquor. Yield: 100 mg, 64%. MS: 628.8 (M+H)+, 626.8. (M−H)− Method ESI+, ESI−

Example 2

7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-[1,8]naphthyridine-3-carboxylic acid

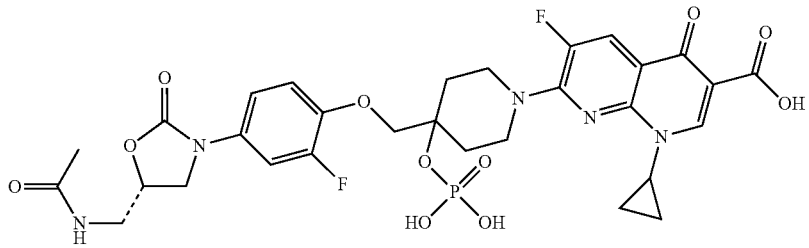 [SMILES: CC(=O)NC[C@H]1CN(c2ccc(OCC3(OP(=O)(O)O)CCN(c4nc5c(cc4F)c(=O)c(C(=O)O)cn5C4CC4)CC3)c(F)c2)C(=O)O1]

Step 1: 7-[4-{4-[(5S)-5-(Acetylamino-methyl)-2-oxo-oxazolidin-3-yl]-2-fluoro-phenoxymethyl}-4-(bis-benzyloxy-phosphoryloxy)-piperidin-1-yl]-1-cyclopropyl-6-fluoro-4-oxo-1,4-dihydro-[1,8]naphthyridine-3-carboxylic acid A suspension of 125 mg 7-(4-{[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-[1,8]naphthyridine-3-carboxylic acid (MW: 627.60, 0.2 mmol) and 42 mg tetrazole (MW: 70.05, 0.6 mmol) in 1 ml dichloromethane was treated with 138 mg of dibenzyl N,N-diisopropylphosphoramidite (MW: 345.42, 0.4 mmol). The original suspension slowly cleared. The solution was stirred at room temperature for two hours and monitored by TLC. (dichloromethane/methanol 9:1). The reaction mixture was cooled to 0° C. and treated with a 0.6 ml of a 0.5M m-chloroperbenzoic acid solution in dichloromethane. The mixture was stirred for two hours at room temperature and diluted with 20 ml dichloromethane. The organic layer was washed successively with 20 ml of a saturated aqueous sodium bicarbonate solution and 20 ml of brine and dried over magnesium sulfate. The slurry was filtered and the filtrate evaporated under reduced pressure. The residue was purified by chromatography over silica using a 9/1 dichloro-methane/methanol mixture as eluent to afford an off white solid. Yield: 158 mg, 89%. MS: 889.3 (M+H)+, 887.0 (M−H)− Method ESI+, ESI−.

Step 2: 7-(4-{4-[(5S)-(5-Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-[1,8]naphthyridine-3-carboxylic acid A suspension of 158 mg 7-[4-{4-[(5S)-5-(Acetylamino-methyl)-2-oxo-oxazolidin-3-yl]-2-fluoro-phenoxymethyl}-4-(bis-benzyloxy-phosphoryloxy)-piperidin-1-yl]-1-cyclopropyl-6-fluoro-4-oxo-1,4-dihydro-[1,8]naphthyridine-3-carboxylic acid (MW: 887.84, 0.177 mmol) and 20 mg of palladium hydroxide 20% on activated carbon in 20 ml of a 6/3/1 dichloromethane/methanol/water mixture was stirred at room temperature under hydrogen for three hours. The catalyst was filtered off using a glass fibre filter paper. The solvents were evaporated under reduced pressure and the residue dissolved in 10 ml methanol. The solution was diluted with 20 ml water while a white solid precipitated. The solid was collected and dried. Yield: 85 mg, 68%. MS: 709.0 (M+H)$^+$, 706.5 (M−H)$^−$ Method ESI$^+$, ESI$^−$.

Example 3

7-[4-{4-[(5S)-5-(Acetylamino-methyl)-2-oxo-oxazolidin-3-yl]-2-fluoro-phenoxymethyl}-4-(2,6-diamino-hexanoyloxy)-piperidin-1-yl]-1-cyclopropyl-6-fluoro-4-oxo-1,4-dihydro-[1,8]naphthyridine-3-carboxylic acid

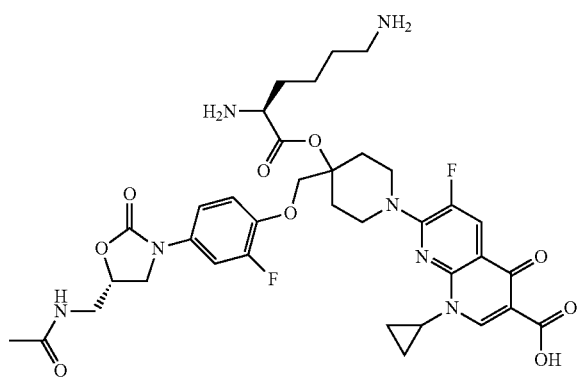 [SMILES: CC(=O)NC[C@H]1CN(c2ccc(OCC3(OC(=O)[C@@H](N)CCCCN)CCN(c4nc5c(cc4F)c(=O)c(C(=O)O)cn5C4CC4)CC3)c(F)c2)C(=O)O1]

Step 1: 4-{4-[(5S)-(5-Acetylamino-methyl)-2-oxo-oxazolidin-3-yl]-2-fluoro-phenoxymethyl}-4-hydroxy-piperidine-1-carboxylic acid tert-butyl ester In analogy of example 1 step 5 by reacting 3.83 g 1-oxa-6-aza-spiro[2.5]octane-6-carboxylic acid tert-butyl ester (WO0204462) (MW: 213.28 18 mmol), 4.02 g N-[(5S)-{3-(3-fluoro-4-hydroxy-phenyl)}-2-oxo-oxazolidin-5-ylmethyl]-acetamide (MW: 268.246, 15 mmol) and 3.1 g potassium carbonate (MW: 138.20, 22.5 mmol) in 30 ml dimethylformamide. Yield: 4.89-g, 67%. MS: 482.6 (M+H)$^+$, Method ESI$^+$.

Step 2: 4-{4-[(5S)-5-(Acetylamino-methyl)-2-oxo-oxazolidin-3-yl]-2-fluoro-phenoxymethyl}-4-(2,6-bis-benzyloxycarbonylamino-hexanoyloxy)-piperidine-1-carboxylic acid tert-butyl ester A suspension of 96 mg of 4-{4-[5-(5S)-(acetylamino-methyl)-2-oxo-oxazolidin-3-yl]-2-fluoro-phenoxymethyl}-4-hydroxy-piperidine-1-carboxylic acid tert-butyl ester (MW: 481.52, 0.2 mmol), 195 mg of Z-Lys (Z)—OH (MW: 414.46, 0.4 mmol) and 49 mg of 4-dimethylaminopyridine (MW: 122.17, 0.4 mmol) in 2 ml dichloromethane was treated under stirring at room temperature with 115 mg N-(3-dimethylaminopropyl)-N'-ethyl-carbodiimid hydrochloride (MW: 191.70, 0.6 mmol). The reaction mixture was stirred over night. The mixture was diluted with 20 ml ethyl acetate and the organic layer washed successively with 10 ml N aqueous hydrochloric acid, 20 ml water and 20 ml brine. The organic layer was dried over magnesium sulfate, filtered and the filtrate evaporated to dryness. The residue was purified by chromatography on silica, using a 9/1 dichloromethane/methanol mixture as eluent to leave a colorless sticky oil. Yield: 150 mg, 88%. MS: 878.8 (M+H)$^+$, Method ESI$^+$.

Step 3: 2,6-Bis-benzyloxycarbonylamino-hexanoic acid 4-{4-[(5S)-5-(acetylamino-methyl)-2-oxo-oxazolidin-3-yl]-2-fluoro-phenoxymethyl}-piperidin-4-yl ester hydrochloride 200 mg of 4-{4-[5-(5S)-(acetylamino-methyl)-2-oxo-oxazolidin-3-yl]-2-fluoro-phenoxymethyl}-4-(2,6-bis-benzyloxycarbonylamino-hexanoyloxy)-piperidine-1-carboxylic acid tert-butyl ester (MW: 977.97, 0.22 mmol) were dissolved in 4 ml of a 1.25M dry hydrochloric acid in methanol. The reaction was stirred at 40° C. for two hours, and the solvent removed by distillation under reduced pressure to leave a off white solid. Yield: 178 mg, quantitative. MS: 778.8 (M+H)$^+$, Method EST$^+$.

Step 4: 7-[4-{4-[(5S)-5-(Acetylamino-methyl)-2-oxo-oxazolidin-3-yl]-2-fluoro-phenoxymethyl}-4-(2,6-bis-benzyloxycarbonylamino-hexanoyloxy)-piperidin-1-yl]-1-cyclopropyl-6-fluoro-4-oxo-1,4-dihydro-[1,8]naphthyridine-3-carboxylic acid In analogy to example 1 step 7, with 62 mg 7-chloro-1-cyclopropyl-6-fluoro-1,4-dihydro-4-oxo-[1,8]naphthyridine-3-carboxylic acid (MW: 282.66, 0.25 mmol), 178 mg 2,6-bis-benzyloxycarbonylamino-hexanoic acid 4-{4-[5-(5S)-(acetyl-amino-methyl)-2-oxo-oxazolidin-3-yl]-2-fluoro-phenoxy-methyl}-piperidin-4-yl ester hydrochloride (MW: 814.31, 0.22 mmol), 90 mg triethylamine (MW: 101.19, 0.88 mmol) and 48 mg trimethylchlorsilan (MW: 108.64, 0.44 mmol) in 1 ml N-methyl-pyrrolidin-2-one. Yield: 94 mg, 42%. MS: 1025.3 (M+H)$^+$, Method ESI$^+$.

Step 5: 7-[4-{4-[(5S)-5-(Acetylamino-methyl)-2-oxo-oxazolidin-3-yl]-2-fluoro-phenoxymethyl}-4-(2,6-diamino-hexanoyloxy)-piperidin-1-yl]-1-cyclopropyl-6-fluoro-4-oxo-1,4-dihydro-[1,8]naphthyridine-3-carboxylic acid A suspension of 94 mg 7-[4-{4-[(5S)-5-(acetylamino-methyl)-2-oxo-oxazolidin-3-yl]-2-fluoro-phenoxymethyl}-4-(2,6-bis-benzyloxycarbonylamino-hexanoyloxy)-piperidin-1-yl]-1-cyclopropyl-6-fluoro-4-oxo-1,4-dihydro-[1,8]naphthyridine-3-carboxylic acid (MW: 1024.05, 0.091 mmol) and 20 mg of palladium hydroxide 20% on activated carbon in 20 ml of a 6/3/1 dichloromethane/methanol/water mixture was stirred at room temperature under hydrogen for four hours. The catalyst was filtered off using a glass fibre filter paper. The solvents were evaporated under reduced pressure and the residue dissolved in 10 ml methanol. The solution was diluted with 20 ml water while a white solid precipitated. The solid was collected and dried. Yield: 29 mg, 43%. MS: 757.0 (M+H)$^+$, 755.2 Method ESI$^+$, ESI$^−$.

Example 4

Succinic acid mono-[4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl] ester

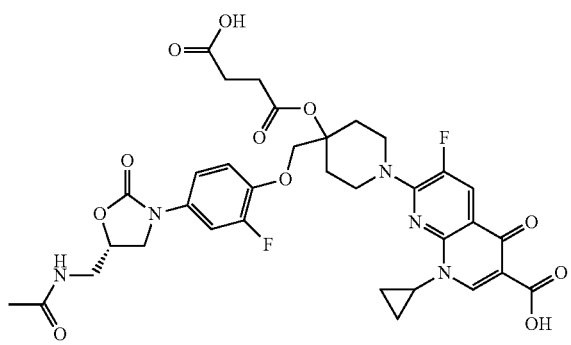 [SMILES: CC(=O)NC[C@H]1CN(c2ccc(OCC3(OC(=O)CCC(=O)O)CCN(c4nc5c(cc4F)c(=O)c(C(=O)O)cn5C4CC4)CC3)c(F)c2)C(=O)O1]

Step 1: Succinic acid 4-{4-[(5S)-5-(acetylamino-methyl)-2-oxo-oxazolidin-3-yl]-2-fluoro-phenoxymethyl}-1-tert-butoxy-carbonyl-piperidin-4-yl ester benzyl ester:

In analogy of example 3 step 2 with 825 mg 4-{4-[(5S)-5-(acetylamino-methyl)-2-oxo-oxazolidin-3-yl]-2-fluoro-phenoxymethyl}-4-hydroxy-piperidine-1-carboxylic acid tert-butyl ester (MW: 481.52, 1.71 mmol), 1.07 g of succinic acid monobenzyl ester (MW: 208.21, 5.14 mmol) and 0.63 g of 4-dimethylaminopyridine (MW: 122.17, 5.1 mmol) in 10 ml dichloromethane was treated under stirring at room temperature with 1.3 g N-(3-dimethylaminopropyl)-N'-ethyl-carbodiimid HCl (MW: 191.70, 6.8 mmol). Yield: 820 mg, 70%. MS: 673.3 (M+H)+, Method ESI+.

Step 2: Succinic acid 4-{4-[(5S)-5-(acetylamino-methyl)-2-oxo-oxazolidin-3-yl]-2-fluoro-phenoxymethyl}-piperidin-4-yl ester benzyl ester 820 mg of succinic acid 4-{4-[(5S)-5-(acetylamino-methyl)-2-oxo-oxazolidin-3-yl]-2-fluoro-phenoxymethyl}-1-tert-butoxy-carbonyl-piperidin-4-yl ester benzyl ester (MW: 671.72, 1.23 mmol) were dissolved in 4 ml of trifluoro acetic acid. The reaction mixture was stirred at room temperature for one hour. The solvent was evaporated, the residue dissolved in 30 ml of a 9/1 dichloromethane/methanol mixture and the organic layer washed successively with 30 ml of a saturated aqueous sodium bicarbonate solution and 30 ml of brine. The organic layer was dried over magnesium sulfate, filtered and the filtrate evaporated under reduced pressure. The residue was purified by chromatography over silica, using a 95/5 dichloromethane/methanol mixture with 2% triethylamine as eluent. Yield: 420 mg, 60%. MS: 572.7 (M+H)+, Method ESI+.

Step 3: Succinic acid 4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl ester benzyl ester In analogy to example 1 step 7, with 113 mg 7-chloro-1-cyclopropyl-6-fluoro-1,4-dihydro-4-oxo-[1,8]naphthyridine-3-carboxylic acid (MW: 282.66, 0.4 mmol), 230 mg succinic acid 4-{4-[(5S)-5-(acetylamino-methyl)-2-oxo-oxazolidin-3-yl]-2-fluoro-phenoxymethyl}-piperidin-4-yl ester benzyl ester (MW: 571.60, 0.4 mmol), 161 mg triethylamine (MW: 101.19, 1.6 mmol) and 87 mg trimethylchlorsilan (MW: 108.64, 0.8 mmol) in 2 ml N-methyl-pyrrolidin-2-one. Yield: 25 mg, 7.6%. MS: 819 (M+H)+, 817.8, Method ESI+, ESI−.

Step 4: Succinic acid mono-[4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl]ester In analogy to example 3 step 5 with 22 mg succinic acid 4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl ester benzyl ester (MW: 817.80, 0.026 mmol) and 2 mg of palladium hydroxide 20% on activated carbon in 20 ml of a 1/1 tetrahydrofuran/methanol mixture. Yield: 16 mg, 81%. MS: 729 (M+H)+, 727 (M+H)−, Method ESI+, ESI−.

Example 5

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid

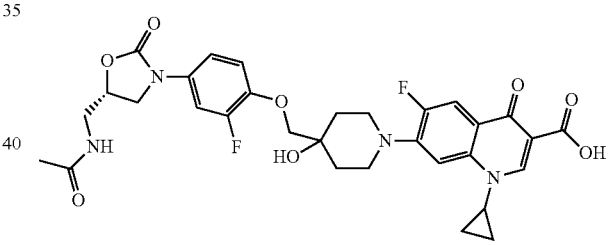

A solution of 60 g N-[{(5S)-3[3-fluoro-4-(4-hydroxy-piperidin-4-ylmethoxy)-phenyl]-2-oxo-oxazolidin-5-ylmethyl}]-acetamide. ($C_{18}H_{24}FN_3O_5$, MW: 381.40 0.157 mole) and 26.87 ml of ethyl diisopropylamine (MW: 129.25, 0.157 mole) in 300 ml N-methyl-pyrrolidin-2-one was treated with 67.81 g (7-chloro-1-cyclopropyl-6-fluoro-1,4-dihydro-4-oxo-3-quinolinecarboxylic acid-boron diacetate complex (MW: 410.57, 0.165 mole) and the mixture was stirred at 80° C. for 5 hours. The N-methyl-pyrrolidin-2-one was evaporated under reduced pressure and residue was dissolved in 300 ml of methanol. Anhydrous hydrogen chloride was bubbled through the solution at 10° C. for 30 minutes. The solution was stirred at room temperature while a yellow solid precipitated. The conversion of the boron complex to the free acid was monitored by HPLC. The mixture was diluted with 300 ml ethyl acetate. The solid was filtered and washed with 100 ml of 8/2 ethyl acetate/methanol and 100 ml of ethyl acetate. The yellow solid was dried to leave 86.4 g of a yellow solid. The solid was dissolved in 200 ml dimethylsulfoxyde at 40° C., and the yellow solution was added under stirring to 1000 ml water. The yellow solid was collected, washed with water and dried. Yield: 73 g, 74.5%. MS: 627.8 (M+H)+, 625.8 (M+H)−, Method ESI+, ESI−.

Example 6

7-[4-{4-[(5S)-5-(Acetylamino-methyl)-2-oxo-oxazo-lidin-3-yl]-2-fluoro-phenoxymethyl}-4-(bis-benzyloxy-phosphoryloxy)-piperidin-1-yl]-1-cyclopropyl-6-fluoro-4-oxo-1,4-dihydro-quinoline-3-carboxylic Acid

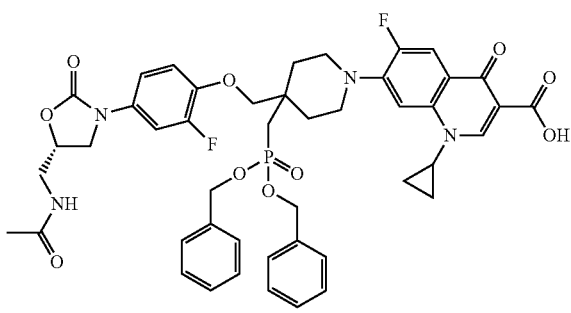 [SMILES: CC(=O)NC[C@H]1CN(c2ccc(OCC3(CP(=O)(OCc4ccccc4)OCc4ccccc4)CCN(c4cc5c(cc4F)c(=O)c(C(=O)O)cn5C4CC4)CC3)c(F)c2)C(=O)O1]

A suspension of 35 g 7-(4-{4-[5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid (MW: 626.61, 55.85 mmol) and 6.45 g tetrazole (MW: 70.05, 92.15 mmol) in 700 ml dichloromethane was treated at room temperature under stirring with a solution of 31.8 g dibenzyldiisopropylphosphoramidit (MW: 345.42, 92.15 mmol) in 20 ml dichloromethane. The reaction was monitored by TLC (dichloromethane/methanol 9:1). The reaction was stirred for one hour and the mixture was washed at 0° C. with 200 ml 1N aqueous hydrochloric acid and 100 ml of a saturated sodium bicarbonate solution. The water layer were backwashed with 200 ml dichloromethane. The combined organic layer were concentrated to 500 ml and treated at room temperature with 13.2 ml of a 70% ter-butyl hydroperoxid solution in water (MW: 90.12, 95 mmol). The reaction was stirred for 30 min, diluted with 500 ml dichloromethane and the organic layer washed with 200 ml N aqueous hydrochloric acid and with 300 ml brine. The organic layer was dried over magnesium sulfate, filtered and the filtrate evaporated under reduced pressure. The residue was dissolved in 400 ml dichloromethane and diluted with 400 ml N-hexane. The mixture was concentrated (300-mbar, 40° C. bath temperature) to a volume of 400 ml. The sticky oil was decanted and dissolved in 400 ml of refluxing methanol. The solution was concentrated to 300 ml under reduced pressure and stirred over night at RT. The slurry was cooled to 0° C. and the solid collected. Yield: 27.60 g, 55.6%. MS: 888.3 (M+H)$^+$, 885.8 (M+H)$^-$, Method ESI$^+$, ESI$^-$.

Example 7

7-(4-{4-[(5S)-5-(Acetylamino-methyl)-2-oxo-oxazo-lidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic Acid

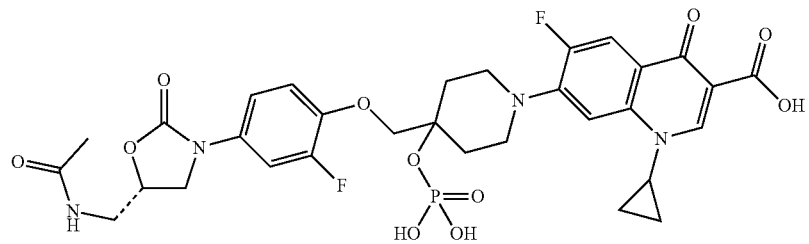

27 g 7-[4-{4-[(5S)-5-(acetylamino-methyl)-2-oxo-oxazolidin-3-yl]-2-fluoro-phenoxymethyl}-4-(bis-benzyloxy-phosphoryloxy)-piperidin-1-yl]-1-cyclopropyl-6-fluoro-4-oxo-1,4-dihydro-quinoline-3-carboxylic acid (MW: 886.85, 30.44 mmol) were suspended in 600 ml acetonitrile and treated with 53 ml of a 33% solution of anhydrous hydrobromic acid in acetic acid. The yellow suspension was diluted with 150 ml of acetic acid and was heated to 45° C. The reaction was monitored by HPLC/MS and was complete after 3 hours.

The sticky suspension was added to 1.5 L of water under stirring. The off white crystals were collected, washed with 300 ml water, 150 ml ethanol and 150 ml ether. The solid was suspended in 1.3 L water and treated with 35 ml (35 mmol) of a 1M aqueous sodium hydroxide solution. The solid dissolved, and the brown-yellow solution was treated with 15 g of activated charcoal and filtered. The filtrate was extracted with 3 portions of 200 ml of a 95/5 dichloromethane/methanol mixture. The water layer was treated with 40 ml of 1 M HCl solution and the product crystallized by stirring. The solid was collected and dried. Yield: 17.3-g, 80.4%. MS: 609.7 (M+H)$^+$, 607.8 (M+H)$^-$, Method ESI$^+$, ESI$^-$.

Example 8

7-(4-{4-[(5S)-5-(Acetylamino-methyl)-2-oxo-oxazo-lidin-3-yl]-2-fluoro-phenoxymethyl}-4-hydroxy-piperidin-1-yl)-1-cyclopropyl-6-fluoro-8-methoxy-4-oxo-1,4-dihydro-quinoline-3-carboxylic acid

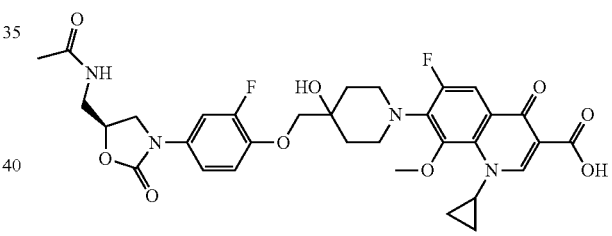

In analogy to example 5 with 114 mg N-[{(5S)-3[3-fluoro-4-(4-hydroxy-piperidin-4-ylmethoxy)-phenyl]-2-oxo-oxazolidin-5-ylmethyl}]-acetamide. (MW: 381.40 0.3 mmol), 127 mg of 1-cyclopropyl-6,7-difluoro-1,4-dihydro-8-methoxy-4-oxo-3-quinolinecarboxylic acid diacetylborate (Sakurai, Nobuhiro; Sano, Mitsuharu; Hirayama, Fumihiro; Kuroda, Tsuyoshi; Uemori, Satoru; Bioorg. Med. Chem. Lett.; 8; 16; 1998; 2185-2190) (MW: 423.137, 0.3 mmol) and 38 mg of ethyl diisopropylamine (MW: 129.25, 0.3 mmol) in 1 ml N-methyl-pyrrolidin-2-one. Yield: 137 mg, 69.5%. MS: 658.2 (M+H)$^+$, 655.8 (M+H)$^-$, Method ESI$^+$, ESI$^-$.

Example 9

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-8-methoxy-4-oxo-1,4-dihydro-quinoline-3-carboxylic Acid

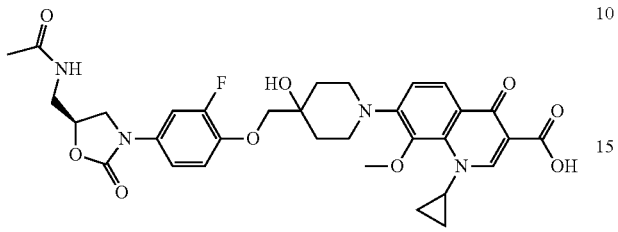

In analogy to example 5 with 114 mg N-[{(5S)-3[3-fluoro-4-(4-hydroxy-piperidin-4-ylmethoxy)-phenyl]-2-oxo-oxazolidin-5-yl-methyl}]-acetamide. (MW: 381.40 0.3 mmol), 121 mg of 1-cyclopropyl-8-methoxy-4-oxo-1,4-dihydro-quinoline-3-carboxylatoboron diacetate (WO03032962) (MW: 405.15, 0.3 mmol) and 77 mg of ethyl diisopropylamine (MW: 129.25, 0.6 mmol) in 2 ml N-methyl-pyrrolidin-2-one. Yield: 117 mg, 61.2%. MS: 639.8 (M+H)$^+$, 637.5 (M+H)$^-$, Method ESI$^+$, ESI$^-$.

Example 10

9-(4-{4-[(5S)-5-(Acetylamino-methyl)-2-oxo-oxazolidin-3-yl]-2-fluoro-phenoxymethyl}-4-hydroxy-piperidin-1-yl)-8-fluoro-3-methyl-6-oxo-2,3-dihydro-6H-1-oxa-3a-aza-phenalene-5-carboxylic Acid

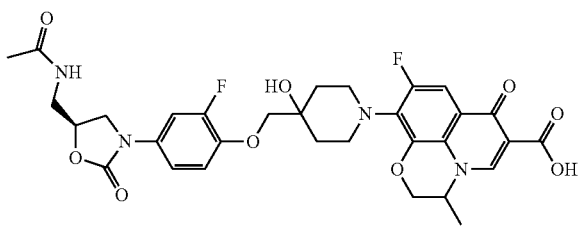 [SMILES: CC(=O)NC[C@H]1CN(c2ccc(OCC3(O)CCN(c4c(F)cc5c(=O)c(C(=O)O)cn6c5c4OCC6C)CC3)c(F)c2)C(=O)O1]

A solution of 140 mg of 9-10-difluoro-2,3-dihydro-3-methyl-7-oxo-7H-pyrido[1,2,3-de]-1,4-benzoxazine-6-carboxilic acid (MW: 281.22, 0.5 mmol), 191 mg of N-[{(5S)-3[3-fluoro-4-(4-hydroxy-piperidin-4-ylmethoxy)-phenyl]-2-oxo-oxazolidin-5-yl-methyl}]-acetamide (MW: 381.40, 0.5 mmol), and 129 mg of ethyl diisopropylamine (MW: 129.25, 1 mmol) was stirred at 80° C. in 1 ml of N-methyl-pyrrolidin-2-one for 24 hours. The solvent was evaporated under reduced pressure. The residue was dissolved in methanol and treated with 10 ml of a 1.2 M anhydrous hydrogen chloride solution in methanol. The methanol was evaporated and the residue digested in ethyl acetate. The solid was collected and crystallized twice from a dichloromethane/ethanol mixture. Yield: 88 mg, 27%. MS: 643.7 (M+H)$^+$, 641.5 (M+H)$^-$, Method ESI$^+$, ESI$^-$.

Example 11

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-[1,8]naphthyridine-3-carboxylic Acid

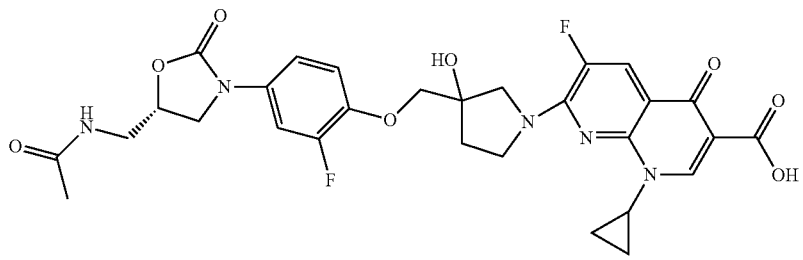 [SMILES: CC(=O)NC[C@H]1CN(c2ccc(OCC3(O)CCN(c4nc5c(cc4F)c(=O)c(C(=O)O)cn5C4CC4)C3)c(F)c2)C(=O)O1]

Step 1: 1-Oxa-5-aza-spiro[2.4]heptane-5-carboxylic acid benzyl ester

A solution 3-methylen-pyrrolidine-1-carboxylic acid benzyl ester (WO9624593) in 5 ml of dichloromethane was treated with 2.16 g sodium bicarbonate (MW: 84.01 26.28 mmol) and 2.47 g of 80% m-chlor-perbenzoic acid (MW: 172.57, 11.48 mmol). The reaction mixture was stirred at room temperature for three hours. The reaction mixture was diluted with 20 ml of a saturated aqueous sodium sulfite solution and 45 ml of dichloromethane. The organic layer was successively washed with 30 ml of an aqueous saturated sodium bicarbonate solution and brine. The organic layer was dried over magnesium sulfate. The residue was purified by chromatography on silica (1/1 ethyl acetate/n-hexane) to afford a off white solid. Yield: 440 mg, 57%. MS: 234.1 (M+H)$^+$, Method ESI$^+$.

Step 2: 3-{4-[(5S)-5-(Acetylamino-methyl)-2-oxo-oxazolidin-3-yl]-2-fluoro-phenoxymethyl}-3-hydroxy-pyrrolidine-1-carboxylic acid benzyl ester A solution of 420 mg of N-[(5S)-{3-(3-fluoro-4-hydroxy-phenyl)}-2-oxo-oxazolidin-5-ylmethyl]-acetamide (MW: 268.246, 1.56 mmol) in 2 ml dimethylformamide was treated with 83 mg sodium hydride. The suspension was stirred for one hour at room temperature. A solution of 440 mg 1-oxa-5-aza-spiro[2.4]heptane-5-carboxylic acid benzyl ester (MW: 233.26, 1.88 mmol) in 1 ml DMF was added and the mixture was stirred at 70° C. for three hours. The dimethylformamide was evaporated under reduced pressure and the residue was purified by chromatography over silica (95/5 dichloromethane/methanol mixture with 1% ammonia) to afford an off white powder. Yield: 630 mg, 80%. MS: 502.5 (M+H)⁺, Method ESI⁺.

Step 3: N-{(5S)-3-[3-Fluoro-4-(3-hydroxy-pyrrolidin-3-yl-methoxy)-phenyl]-2-oxo-oxazolidin-5-ylmethyl}-acetamide A suspension of 660 mg 3-{4-[(5S)-5-(acetylamino-methyl)-2-oxo-oxazolidin-3-yl]-2-fluoro-phenoxymethyl}-3-hydroxy-pyrrolidine-1-carboxylic acid benzyl ester (MW: 501.51, 1.31 mmol) and 20 mg palladium 10% on activated carbon in 20 ml of a 1/1 ethyl acetate/methanol mixture was stirred for twelve hours under hydrogen. The catalyst was filtered on a glass fiber filter paper and the filtrate evaporated under reduced pressure to afford a colorless oil. Yield: 400 mg, 83.2%. MS: 368.4 (M+H)⁺, Method ESI⁺.

Step 4: 7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-[1,8]naphthyridine-3-carboxylic acid In analogy to example 1, step 7 with 39 mg 7-chloro-1-cyclo-propyl-6-fluoro-1,4-dihydro-4-oxo-[1,8]naphthyridine-3-carboxylic acid (MW: 282.66, 0.24 mmol), 99 mg N-{(5S)-3-[3-fluoro-4-(3-hydroxy-pyrrolidin-3-yl-methoxy)-phenyl]-2-oxo-oxazolidin-5-ylmethyl}-acetamide. (MW: 367.38, 0.24 mmol) 101 mg triethylamine (MW: 101.19, 1.0 mmol) and 80 mg trimethylchlorsilan (MW: 108.64, 0.75 mmol) in 2 ml N-methyl-pyrrolidin-2-one. Yield: 70 mg, 46%. MS: 614.7 (M+H)⁺, 612.7 (M+H)⁻, Method ESI⁺, ESI⁻.

Example 12

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-quinoline-3-carboxylic acid

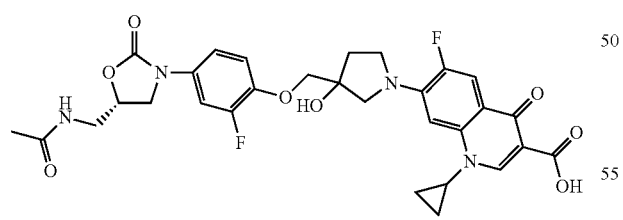

In analogy to example 5 with 106 mg N-{(5S)-3-[3-fluoro-4-(3-hydroxypyrrolidin-3-ylmethoxy)-phenyl]-2-oxo-oxazolidin-5-ylmethyl}-acetamide. (MW: 367.38, 0.29 mmol) 119 mg (7-chloro-1-cyclopropyl-6-fluoro-1,4-dihydro-4-oxo-3-quinolinecarboxylic acid-boron diacetate complex (MW: 410.57, 0.29 mmol) and 75 mg of ethyl diisopropylamine (MW: 129.25, 0.58 mmol) in 2 ml N-methyl-pyrrolidin-2-one. Yield: 19 mg, 11%. MS: 613.5 (M+H)⁺, 611.5 (M+H)⁻, Method ESI⁺, ESI⁻.

Example 13

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-8-methoxy-4-oxo-1,4-dihydro-quinoline-3-carboxylic Acid

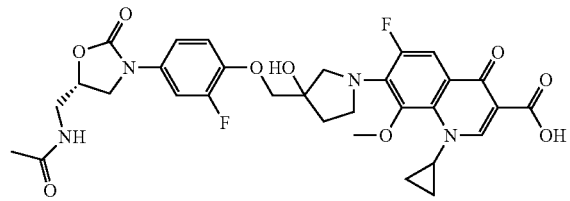 [SMILES: COc1c(N2CCC(O)(COc3ccc(N4C[C@H](CNC(C)=O)OC4=O)cc3F)C2)c(F)cc2c(=O)c(C(=O)O)cn(C3CC3)c12]

In analogy to example 5 with 143 mg N-{(5S)-3-[3-fluoro-4-(3-hydroxy-pyrrolidin-3-ylmethoxy)-phenyl]-2-oxo-oxazolidin-5-ylmethyl}-acetamide (MW: 367.38, 0.39 mmol), 165 mg of 1-cyclopropyl-6,7-difluoro-1,4-dihydro-8-methoxy-4-oxo-3-quinolinecarboxylic acid diacetylborate (MW: 423.137, 0.39 mmol) and 100 mg of ethyl diisopropylamine (MW: 129.25, 0.78 mmol) in 2 ml N-methyl-pyrrolidin-2-one, Yield: 143 mg, 57%. MS: 643.7 (M+H)⁺, 641.7 (M+H)⁻, Method ESI⁺, ESI⁻.

Example 14

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-8-methoxy-4-oxo-1,4-dihydro-quinoline-3-carboxylic Acid

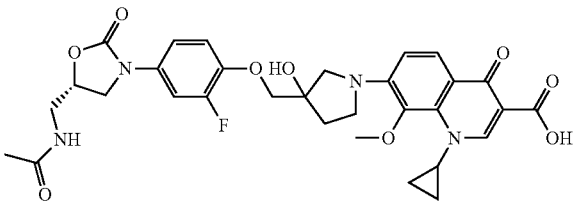 [SMILES: COc1c(N2CCC(O)(COc3ccc(N4C[C@H](CNC(C)=O)OC4=O)cc3F)C2)ccc2c(=O)c(C(=O)O)cn(C3CC3)c12]

In analogy to example 5 with 48 mg N-{(5S)-3-[3-fluoro-4-(3-hydroxy-pyrrolidin-3-ylmethoxy)-phenyl]-2-oxo-oxazolidin-5-ylmethyl}-acetamide (MW: 367.38, 0.13 mmol), 53 mg of 1-cyclopropyl-8-methoxy-4-oxo-1,4-dihydro-quinoline-3-carboxylatoboron diacetate (MW: 405.15, 0.13 mmol) and 33 mg of ethyl diisopropylamine (MW: 129.25, 0.26 mmol) in 1 ml N-methyl-pyrrolidin-2-one. Yield: 41 mg, 50%. MS: 625.8 (M+H)⁺, 623.8 (M+H)⁻, Method ESI⁺, ESI⁻.

Example 15

9-(3-{4-[(5S)-5-(Acetylamino-methyl)-2-oxo-oxazolidin-3-yl]-2-fluoro-phenoxymethyl}-3-hydroxy-pyrrolidin-1-yl)-8-fluoro-3-methyl-6-oxo-2,3-dihydro-6H-1-oxa-3a-aza-phenalene-5-carboxylic Acid

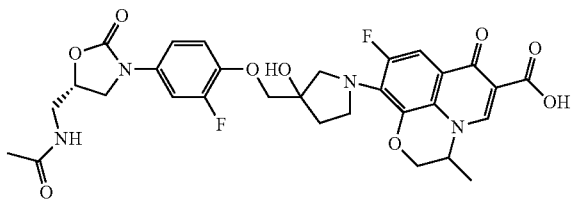 [SMILES: CC(=O)NC[C@H]1CN(c2ccc(OCC3(O)CCN(c4c(F)cc5c(=O)c(C(=O)O)cn6c5c4OCC6C)C3)c(F)c2)C(=O)O1]

In analogy to example 10 with 110 mg of 9-10-difluoro-2,3-dihydro-3-methyl-7-oxo-7H-pyrido[1,2,3-de]-1,4-benzoxazine-6-carboxilic acid (MW: 281.22, 0.39 mmol), 143 mg of N-{(5S)-3-[3-fluoro-4-(3-hydroxy-pyrrolidin-3-yl-methoxy)-phenyl]-2-oxo-oxazolidin-5-ylmethyl}-acetamide. (MW: 367.38, 0.39 mmol), and 100 mg of ethyl diisopropylamine (MW: 129.25, 0.78 mmol) in 2 ml of N-methyl-pyrrolidin-2-one. Yield: 103 mg, 42%. MS: 629.8 (M+H)$^+$, Method ESI$^+$.

Example 16

7-(4-{4-[(5S)-5-(Acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-quinoline-3-carboxylic Acid

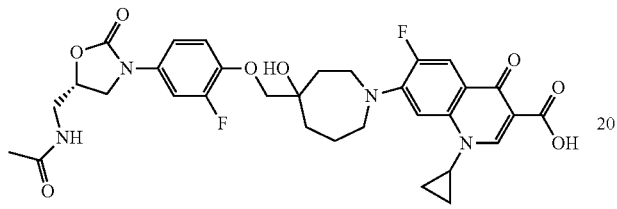

Step 1: 4-Methylene-azepane-1-carboxylic acid tert-butyl ester

A solution of 1 g methyltriphenylphosphoniumbromide (MW: 357.22, 2.79 mmol) in 20 ml of tetrahydrofuran was treated at −78° C. with 1.22 ml of a 2.3 M n-butyl lithium solution in N-hexane (2.8 mmol). The reaction mixture was stirred at −78° C. for ten minutes, then at 0° C. for one hour. The yellow suspension was cooled to −78° C. and treated with a solution of 595 mg 4-oxo-azepane-1-carboxylic acid tert-butyl ester (WO 2000044376) (MW: 213.279, 2.78 mmol) in 10 ml tetrahydrofuran. The reaction mixture was stirred at room temperature for one and half hour. The reaction mixture was quenched with 30 ml of a saturated aqueous solution of ammonium chloride, diluted with 30 ml of ethyl acetate. The organic layer was successively washed with 30 ml water and 30 ml brine, dried over magnesium sulfate and filtered. The filtrate was evaporated under reduced pressure and the residue purified by chromatography over silica. (cyclohexane:ethyl acetate 1:1). Yield: 487 mg, 83%. NMR (CDCl$_3$): 1.35 ppm (s, 9H, tert-but.); 1.6 ppm (m, 2H, —CH$_2$—), 2.14 ppm (m, 2H), 2.33 ppm (m, 2H); 3.29 ppm (m, 4H, N—CH$_2$); 4.67 ppm (m, 2H, vinyl-CH$_2$).

Step 2: 1-Oxa-6-aza-spiro[2.6]nonane-6-carboxylic acid tert-butyl ester

In analogy to example 11 step 1 with 4-methylene-azepane-1-carboxylic acid tert-butyl ester (MW: 211.307, 1.73 mmol), 1.16 g sodium bicarbonate (MW: 84.01 13.8 mmol) and 1.36 g of 80% m-chloroperbenzoic acid (MW 172.57, 6.05 mmol) in 5 ml of dichloromethane. Yield: 250 mg, 63%. MS: 228.8 (M+H)$^+$, 127.8 (M−(CH$_3$)$_3$COCO) method ESI$^+$.

Step 3: 4-{4-[(5S)-5-(Acetylamino-methyl)-2-oxo-oxazolidin-3-yl]-2-fluoro-phenoxymethyl}-4-hydroxy-azepane-1-carboxylic acid tert-butyl ester In analogy to example 1 step 5 with 247 mg of 1-oxa-6-aza-spiro[2.6]nonane-6-carboxylic acid tert-butyl ester. (MW: 227.31 1.08 mmol), 296 mg N-[(5S)-{3-(3-fluoro-4-hydroxy-phenyl)}-2-oxo-oxazolidin-5-ylmethyl]-acetamide (MW: 268.246, 80 mmol) and 228 mg potassium carbonate (MW: 138.20, 1.65 mmol) in 150 ml dimethylformamide. Yield: 334 mg, 62%. MS: 496.8 (M+H)$^+$, 440.8 (M−C(CH$_3$)$_3$+H)$^+$, Method ESI$^+$.

Step 4: N-{(5S)-3-[3-Fluoro-4-(4-hydroxy-azepan-4-ylmethoxy)-phenyl]-2-oxo-oxazolidin-5-ylmethyl}-acetamide A solution of 334 mg 4-{4-[(5S)-5-(acetylamino-methyl)-2-oxo-oxazolidin-3-yl]-2-fluoro-phenoxymethyl}-4-hydroxy-azepane-1-carboxylic acid tert-butyl ester (MW: 495.55, 0.674 mmol) in 3 ml of a 1.25 M anhydrous hydrogen chloride solution in methanol was stired at 35° C. for four hours. The solvent was evaporated under reduced pressure. The residue was dissolved in 4 ml water and the water layer neutralized to pH 7 with a saturated sodium bicarbonate solution. The water was evaporated and the residue dissolved in 30 ml of a 9/1 dichloromethane/methanol mixture. The unsoluble salt were filtered and the filtrate evaporated to dryness to afford off white solid. Yield 266 mg, quant. MS: 395.8 (M+H)$^+$, 440.6 (M+HCOO$^-$), Method ESI$^+$, ESI$^-$.

Step 5: 7-(4-{4-[(5S)-5-(Acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-quinoline-3-carboxylic acid In analogy to example 5 with 150 mg N-{(5S)-3-[3-fluoro-4-(4-hydroxy-azepan-4-ylmethoxy)-phenyl]-2-oxo-oxazolidin-5-ylmethyl}-acetamide (MW: 395.43) and 98 mg of ethyl diisopropylamine (MW: 129.25, 0.758 mmol), 163 mg (7-chloro-1-cyclopropyl-6-fluoro-1,4-dihydro-4-oxo-3-quinolinecarboxylic acid-boron diacetate complex (MW: 410.57, 0.397 mmol) in 2 ml N-methyl-pyrrolidin-2-one. Yield: 70 mg, 28.8%. MS: 641.7 (M+H)$^+$, method ESI$^+$.

Example 17

7-(4-{4-[(5S)-5-(Acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-[1,8]naphthyridine-3-carboxylic Acid

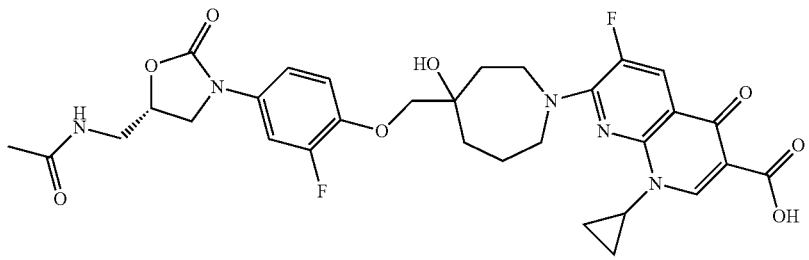 [SMILES: CC(=O)NC[C@H]1CN(c2ccc(OCC3(O)CCCN(c4nc5c(cc4F)c(=O)c(C(=O)O)cn5C4CC4)CC3)c(F)c2)C(=O)O1]

In analogy to example 1 step 7 with 98 mg 7-chloro-1-cyclopropyl-6-fluoro-1,4-dihydro-4-oxo-[1,8]naphthyridine-3-carboxylic acid (MW: 282.66, 0.348 mmol), 138 mg N-{(5S)-3-[3-fluoro-4-(4-hydroxy-azepan-4-ylmethoxy)-phenyl]-2-oxo-oxazolidin-5-ylmethyl}-acetamide (MW: 395.43, 0.348 mmol), 140 mg triethylamine (MW: 101.19, 1.39 mmol) and 113 mg trimethylchlorsilan (MW: 108.64, 1.04 mmol) in 1 ml N-methyl-pyrrolidin-2-one. Yield: 150 mg, 77%. MS: 642.7 (M+H)$^+$, 640.7 (M+H)$^-$, Method ESI$^+$, ESI$^-$.

Example 18

Sodium Salt of 7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid 183 g of the compound of example 7 were dissolved in 400 mL dry DMSO at room temperature. Then the solution was treated with 60 g Fullers earth and filtered off. The remaining solid was washed with 50 mL dry DMSO. The combined filtrates were mixed with another 50 mL of dry DMSO and 2000 mL of dry acetone under nitrogen. To this solution a solution of 47.1 g sodium-2-ethylhexanoate (97% in ethyl acetate, i.e. 250 mL) was added drop wise at room temperature. The resulting suspension was then stirred for 1 h, followed by the addition of 2750 mL ethyl acetate at room temperature. The resulting suspension was stirred for another hour and the resulting crystals were collected by filtration, washing the solid with ethyl acetate (10×500 ml) to remove the DMSO and then dried in vacuo. If there is still amounts of DMSO and/or ethyl acetate remaining, then the solid was slurred with acetone/water (99:1) for 24 h. The mixture was then filtered, washed with acetone/water (99:1) (2×500 ml) and then allowed to suck dry on the filter for 12 h. The solid was then dried in vacuo. Yield: 90%.

Example 19

Formation of Building Blocks via a Sonogashira Reaction—4-{4-[5S-(acetylamino-methyl)-2-oxo-oxazolidin-3-yl]-2-fluoro-phenylethynyl}-4-hydroxy-piperidine-1-carboxylic Acid Tert-Butyl Ester

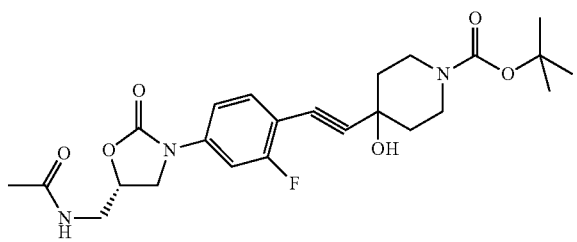 [SMILES: CC(=O)NC[C@H]1CN(c2ccc(C#CC3(O)CCN(C(=O)OC(C)(C)C)CC3)c(F)c2)C(=O)O1]

Step 1: (4-Bromo-3-Fluoro-phenyl)-carbamic acid benzyl ester.

Sodium hydrogen carbonate (27.63 g, 0.329 mol, 1.25 eq) and a saturated solution of sodium hydrogen carbonate (333 ml) were added to a stirred solution of 4-bromo-3-fluoroaniline (50.0 g, 0.263 mol, leg) in acetone (660 ml). The resulting mixture was cooled to 15° C. and benzyl chloroformate (39 ml, 0.276 mol, 1.05 eq) was added gradually, taking care that the reaction temperature did not exceed 22° C. The mixture was stirred over 90 mins at room temperature and the acetone was removed under vacuum. The aqueous layer was then extracted with ethyl acetate (3×150 ml). The combined organic layers were then washed with a saturated sodium chloride solution, and dried over MgSO$_4$. After filtration, the solvent was removed, and n-hexane added. The mixture was stirred during 30 min at room temperature, the crystals were filtrated and washed with hexane to give the first crop of solid. The filtrate was evaporated, and the solid mixed with heptane at 0° C. and stirred during 30 min. The product was again filtered, to give the second crop of solid. The two crops were then combined, to give the product (85.3 g, quantitative) as of solid.

Step 2: (5R)3-(4-Bromo-3-Fluoro-phenyl)-5-hydroxymethyl oxazolidin-2-one

Butyl lithium (2.3M in n-hexanes, 118.3 ml, 0.272 mol, 1.06 eq) was added at −30° C. to anhydrous tert-butanol (25.0 g, 0.53 mol, 2.07 eq) in anhydrous THF (170 ml), under nitrogen. The mixture was stirred for 30 min at −30° C., and was then allowed to warm slowly to 0° C. After 30 min at 0° C., the (4-bromo-3-fluoro-phenyl)-carbamic acid benzyl ester (83 g, 0.256 mol, 1 eq) was added portionwise, keeping the temperature cold, and the mixture was stirred for an additional 30 min at 0° C. To this ice cold mixture, R(−)-glycidyl butyrate (39.7 ml, 0.288 mol, 1.12 eq) were added and the mixture allowed to come gradually to room temperature. The mixture was extracted with saturated sodium chloride solution and the organic phase was dried over MgSO$_4$, filtrated and evaporated. The product was obtained after recrystallisation of the crude product with ethyl acetate, to give (64.1 g, 86.4%).

Step 3: Methanesulfonic acid 3-(4-Bromo-3-Fluoro-phenyl)-2-oxo-oxazolidin-(5R)-ylmethyl ester Methansulfonyl chloride (27.4 ml, 0.354 mol, 1.9 eq) was added to an ice-cold solution of the (5R) 3-(4-Bromo-3-Fluoro-phenyl)-5-hydroxymethyl oxazolidin-2-one (54.0 g, 0.186 mol, 1 eq) and triethylamine (51.8 ml, 0.372 mol, 2 eq) in anhydrous DCM (420 ml) at 0° C. The resulting solution was allowed to come to room temperature, and then stirred over 3 hours. The mixture was then washed with 10% sodium hydrogen carbonate solution giving a precipitate. The solid was filtered. The washed with DCM, and the filtrate and washings dried over MgSO$_4$. After filtering, the solvent was removed, and the resulting solid was slurried with diethyl ether. The solid was then filtered, washed with ice cold diethyl ether and dried to give the product (68.5 g, quantitative).

Step 4: (5R)-Azidomethyl-3-(4-Bromo-3-Fluoro-phenyl) oxazolidin-2-one

A suspension of the Methanesulfonic acid 3-(4-Bromo-3-Fluoro-phenyl)-2-oxo-oxazolidin-(5R)-ylmethyl ester (68.5 g, 0.186 mol, 1 eq), tetrabutyl ammonium iodide (0.686 g, 0.00186 mol, 0.01 eq) and sodium azide (24.57 g, 0.378 mol, 2.03 eq) in anhydrous DMF (500 ml) was stirred 80° C. under nitrogen over night. The reaction was cooled, the DMF evaporated and the residue dissolved in ethyl acetate, washed with water and saturated sodium chloride and dried over MgSO$_4$. After filtering, the filtrate was evaporated to give the product (58.6 g, quantitative) as a white solid.

Step 5: (5R)-Aminomethyl-3-(4-Bromo-3-Fluoro-phenyl)oxazolidin-2-one

A mixture of the (5R)-Azidomethyl-3-(4-Bromo-3-Fluoro-phenyl)oxazolidin-2-one (10.5 g, 33.3 mmol, 1 eq), triphenylphosphine (12.6 g, 48 mmol, 1.44 eq) and water (7.8 ml, 433 mmol, 13 eq) in THF (180 ml) were stirred at 80° C. Once the reaction was finished, it was cooled and then the solvents were removed under vacuum. The residue was purified by chromatography (ethyl acetate first to remove the triphenylphosphine derivatives and then with dichloromethane/methanol 9/1) to give the product (9.63 g, quantitative) as a white solid.

Step 6: (5S)—N-[(4-bromo-3-Fluoro-phenyl)-2-oxo-oxazolidin-5-ylmethyl]-acetamide To the (5R)-Aminomethyl-3-(4-Bromo-3-Fluoro-phenyl)oxazolidin-2-one (9.63 g, 33.3 mmol, 1 eq) was added acetic acid (9 ml, 156 mmol, 4.68 eq) and acetic anhydride(9 ml, 95.3 mmol, 2.86 eq). The suspension was stirred at room temperature for 1 h and then the solvent was removed under high vacuum, to give the product (11.03 g, quantitative) as a beige solid.

Step 7: 4-oxo-piperidine-1-carboxylic acid tert-butyl ester

A solution of BOC$_2$O (6.02 g, 27.6 mmol, 1.1 eq) in dioxane (25 ml) was added to 4-Piperidone hydrochloride hydrate (3.9 g, 25.4 mmol, 1 eq) in water/dioxane (50 ml, 1/1). The reaction was exothermic during the addition, and after the addition was finished the reaction was stirred for 4 h at room temperature. The dioxane was evaporated and the resulting residue was extracted in ethyl acetate and then dried over MgSO$_4$. After filtering, the filtrate was evaporated down to give the product (5.06 g, quantitative) as a white solid

Step 8: 4-Hydroxy-4-trimethylsilanylethynyl piperidine-1-carboxylic acid tert-butyl ester n-Butyl lithium (2.3M solution in n-hexanes, 16.0 ml, 36.8 mmol, 1.1 eq) was added to a solution of TMS-alkyne (6.03 ml, 42.4 mmol, 1.26 eq) in THF (124 ml) at −78° C. under nitrogen. The resulting mixture was stirred at −78° C. for a further 30 min, and then a solution of 4-oxo-piperidine-1-carboxylic acid tert-butyl ester (6.7 g, 33.6 mmol, 1 eq) in THF (30 mL) was added at −78° C. The reaction mixture was stirred 15 minutes at 78° C., and then was allowed to warmed up gradually to room temperature. After 30 min, adding 10% sodium hydrogen sulfate quenched the reaction. The two phases were separated and the aqueous layer was back extracted with ethyl acetate. The combined organic layers were washed with brine and dried over magnesium sulfate. After concentration, the pale yellow residue (7 g, 70%) was found pure enough to be carried on without further purification.

Step 9: 4-Ethynyl-4-Hydroxy-piperidine-1-carboxylic acid tert-butyl ester

A mixture of the 4-Hydroxy-4-trimethylsilanylethynyl piperidine-1-carboxylic acid tert-butyl ester (7 g, 23.5 mmol, 1 eq) and potassium carbonate (1.0 g, 7.25 mmol, 0.3 eq) in MeOH (30 ml) were stirred for 6 h at room temperature. After this time, the solvent was removed under reduced pressure and the residue suspended in diethyl ether. The suspension was washed with saturated ammonium chloride and water and dried over MgSO$_4$. After filtering, the filtrate was evaporated to give the product (4.5 g, 86%) as a white solid.

Step 10: 4-{4-[5S-(acetylamino-methyl)-2-oxo-oxazolidin-3-yl]-2-fluoro-phenylethynyl}-4-hydroxy-piperidine-1-carboxylic acid tert-butyl ester PdCl$_2$(P(C$_6$H$_5$)$_3$)$_2$ (297 mg, 0.422 mmol, 0.1 eq) and 148 mg of copper (I) iodide (160 mg, 0.78 mmol, 0.2 eq) were stirred at RT, under argon. Then the (5S)—N-[(4-bromo-3-Fluoro-phenyl)-2-oxo-oxazolidin-5-ylmethyl]-acetamide (1.40 g, 4.22 mmol, 1 eq), 4-Ethynyl-4-Hydroxy-piperidine-1-carboxylic acid tert-butyl ester (1.24 g, 5.5 mmol, 1.3 eq) in anhydrous DMF (20 ml) and diisopropylamine (10 ml) were added. The mixture was stirred at RT during 30 min. As the reaction didn't start, the mixture was heated at 50° C. during one night under stirring. Water and diethyl ether were added, the two layers separated, and the water layer was back extracted with diethyl ether. The combined organic extracts were then washed with saturated sodium chloride solution and dried over MgSO$_4$. After filtering, the filtrate was evaporated and the residue was purified by chromatography (first with ethyl acetate—in order to eliminate the triphenylphosphine residues and then with Dichloromethane/MeOH) to give the product (1.55 g, 77%) as a gray solid

Example 20

Formation of Building Blocks via a Heck Reaction—4-(3-{4-[5S-(acetylamino-methyl)-2-oxo-oxazolidin-3-yl]-2-fluoro-phenyl}-acryloyl)-piperazine-1-carboxylic Acid Tert Butyl Ester

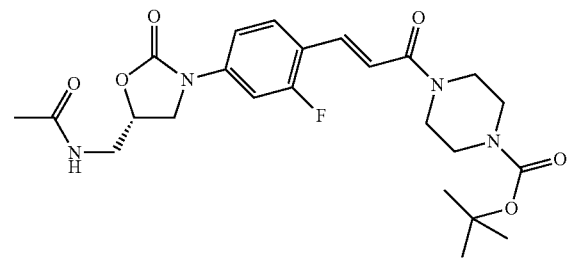 [SMILES: CC(=O)NC[C@H]1CN(c2ccc(/C=C/C(=O)N3CCN(C(=O)OC(C)(C)C)CC3)c(F)c2)C(=O)O1]

Step 1: Piperazine-1-carboxylic acid tert butyl ester

A solution of 24 g of di-tert-butyl dicarbonate (24 g, 0.11 mol, 1 eq) in 200 ml dichloromethane (200 ml) was added to a stirred solution of 20 g piperazine (20 g, 0.23 mol, 2 eq) in dichloromethane (800 ml) at RT. The mixture was stirred overnight at RT and the mixture was then filtered and the filtrate was evaporated. Diethylether was then added to the residue, and the mixture was filtered again, and to the filtrate n-heptane was added. The suspension was filtrated again and the filtrate was evaporated to give the product (19 g, 43.9%) as a white solid.

Step 2: 4-Acryloyl-piperazine-1-carboxylic acid tert butyl ester

Acryloylchlorid (0.8 ml, 9.8 mmol, 1 eq) was added dropwise to a stirred ice-cold solution of piperazine 1-carboxylic acid tert butyl ester (2 g, 9.8 mmol, 1 eq) and triethylamine (1.4 ml, 9.8 mmol, 1 eq) in dichloromethane (50 mL) at 0° C. The mixture was then stirred and allowed to come to room temperature over 2 hours. 1M Hydrochloric acid solution (50 mL) was added to the mixture, and the two layers were separated. The organic phase was washed with saturated sodium hydrogen carbonate solution (2×50 ml) and saturated sodium chloride solution (50 ml) and dried over MgSO$_4$. After filtration, the solvent is evaporated. The residue was purified by chromatography (ethyl acetate/n-hexane 1/1) to give the product (1.26 g, 49%) as a white solid.

Step 3: 4-(3-{4-[5S-(acetylamino-methyl)-2-oxo-oxazolidin-3-yl]-2-fluoro-phenyl}-acryloyl)-piperazine-1-carboxylic acid tert butyl ester (5S)—N-[(4-bromo-3-Fluoro-phenyl)-2-oxo-oxazolidin-5-ylmethyl]-acetamide (1.998 g, 6.0 mmol, 1 eq), 4-Acryloyl-piperazine-1-carboxylic acid tert butyl ester (1.6 g, 6.6 mmol, 1.1 eq) triphenylphosphine (105 mg, 0.4 mmol, 0.067 eq), Palladium (II) acetate (134 mg, 0.6 mmol, 0.1 eq), diisopropylethylamine (10 ml), Potassium carbonate (829 mg, 6 mmol, 1 eq) in DMF (15 ml) were stirred at 140° C. during 4 hours. The solvent was evaporated and the residue was dissolved in dichloromethane, washed with water, dried over MgSO$_4$ and evaporated again. The residue was purified by chromatography (first with ethyl acetate—in order to eliminate the triphenylphosphine residues and then with Dichloromethane/MeOH) to give the product (1.3 g, 46%) as a grey solid Example 21

Formation of Building Blocks via Epoxide Ring Opening with a Phenol-4-(3-{4-[5S-(acetylamino-methyl)-2-oxo-oxazolidin-3-yl]-2-fluoro-phenoxy}-2-hydroxy-propionyl)-piperazine-1-carboxylic Acid Tert Butyl Ester

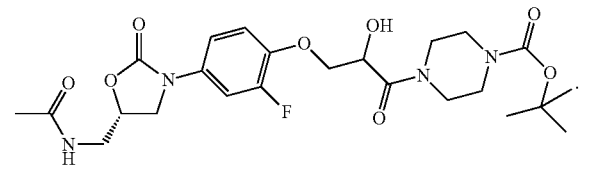 [SMILES: CC(=O)NC[C@H]1CN(c2ccc(OCC(O)C(=O)N3CCN(C(=O)OC(C)(C)C)CC3)c(F)c2)C(=O)O1]

Step 1: 4-Oxiranecarbonyl piperazine-1-carboxylic acid tert butyl ester

A solution of anhydrous t-butyl hydroperoxide (5.5M in nonane, 2.07 ml, 11.38 mmol, 1.5 eq) was added to anhydrous THF (50 mL), at −78° C. under argon. To the resulting solution at −78° C. was added butyl lithium (2.3M in n-hexane, 3.36 ml, 8.4 mmol, 1.1 eq) was added and the solution is stirred for a further 5 min at this temperature. A solution of the 4-Acryloyl-piperazine-1-carboxylic acid tert butyl ester (1.96 g, 7.64 mmol, 1 eq) in anhydrous THF (20 ml) was then added dropwise at −78° C. The resulting mixture was then allowed to warm slowly to room temperature and stirred for a further 16 hr. To the mixture was then added sodium sulfite (1.5 g, 12 mmol, 1.55 eq) and this was then stirred for 15 min. The mixture was then diluted with diethylether (50 ml), filtered through celite and the filtrate evaporated. The residue was purified by chromatography (ethyl acetate/n-hexane 4/1) to give the product (0.39 g, 19%) as a white solid.

Step 2: 4-(3-{4-[5S-(acetylamino-methyl)-2-oxo-oxazolidin-3-yl]-2-fluoro-phenoxy}-2-hydroxy-propionyl)-piperazine-1-carboxylic acid tert butyl ester The 4-Oxiranecarbonyl piperazine-1-carboxylic acid tert butyl ester (0.1 g, 0.39 mmol, 1 eq) was added to a stirred solution of N-[5S)-{3-(3-fluoro-4-hydroxy-phenyl)}-2-oxo-oxazolidin-5-ylmethyl]-acetamide (step 4, example 1) (0.104 g, 0.39 mmol, 1 eq) and K$_2$CO$_3$ (0.081 g, 0.585 mmol, 1.5 eq) in DMF (2 ml). The mixture was heated to 80° C. and then stirred for 4 hours. This was then cooled down to room temperature and then dichloromethane/methanol (10 ml, 9/1) added. The organic layer was then washed with water (2×10 ml) and saturated sodium chloride solution, and then dried over MgSO$_4$. This was then filtered and the solvent is evaporated. The residue was purified by chromatography (dichloromethane/methanol 9/1) to give the product (0.08 g, 39%) as a white solid.

Example 22

Formation of Building Blocks via Alkylation of a Phenol Group—4-(2-{4-[5S-(acetylamino-methyl)-2-oxo-oxazolidin-3-yl]-2-fluoro-phenoxy}-acetyl)-piperazine-1-carboxylic Acid Tert Butyl Ester

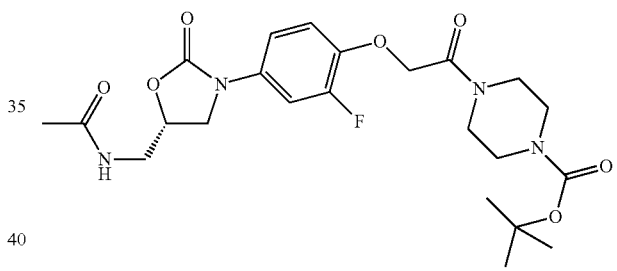

Step 1: 4-(2-bromo acetyl)-piperazine-1-carboxylic acid tert butyl ester

Bromo acetyl bromide (4.86 ml, 21.47 mmol, 1 eq) was added dropwise to a stirred ice cold mixture of the Piperazine-1-carboxylic acid tert butyl ester (4.0 g, 21.47 mmol, 1 eq) and diisopropyl ethyl amine (12.05 g, 92.5 mmol, 4.3 eq) in dichloromethane (108 ml). The resulting mixture was washed with water (2×50 mL) and saturated sodium chloride solution (100 mL), and dried over MgSO$_4$. After filtration, the solvent was evaporated and the residue was purified with chromatography with (ethyl acetate/n-hexane 1/1) to give the product (2.72 g, 41%) as a orange oil.

Step 2: 4-(2-{4-[5S-(acetylamino-methyl)-2-oxo-oxazolidin-3-yl]-2-fluoro-phenoxy}-acetyl)-piperazine-1-carboxylic acid tert butyl ester The 4-(2-bromo acetyl)-piperazine-1-carboxylic acid tert butyl ester (2.0 g, 6.5 mmol, 1 eq) was added to a stirred solution of N-[(5S)-{3-(3-fluoro-4-hydroxy-phenyl)}-2-oxo-oxazolidin-5-ylmethyl]-acetamide (step 4, example 1) (1.75 g, 6.5 mmol, 1 eq) and potassium carbonate (1.138 g, 9.75 mmol, 1.5 eq) in DMF (32 ml). The resulting mixture was heated to 80° C. and stirred for 30 min, then cooled and dichloromethane/methanol (100 ml, 9/1) added. The organic layer was then washed with water (2×10 ml) and saturated sodium chloride solution, and then dried over MgSO$_4$. This was then filtered and the solvent is evaporated. The residue was purified by chromatography (dichloromethane/methanol 9/1) to give the product (1.72 g, 55%) as a brown solid.

Example 23

Formation of Building Blocks via Triple Bond Reduction 4-(2-{4-[5S-(acetylamino-methyl)-2-oxo-oxazolidin-3-yl]-2-fluoro-phenyl}-ethyl)-4-hydroxy-piperidine-1-carboxylic Acid Tert Butyl Ester

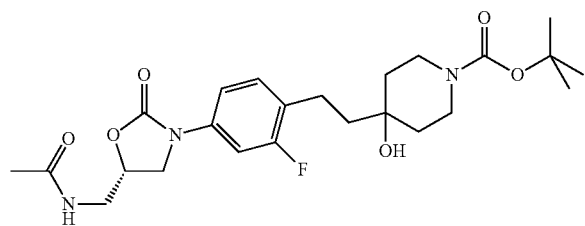 [SMILES: CC(=O)NC[C@H]1CN(c2ccc(CCC3(O)CCN(C(=O)OC(C)(C)C)CC3)c(F)c2)C(=O)O1]

10% Pd/C (100 mg) was added a stirred solution of the 4-{4-[5S-(acetylamino-methyl)-2-oxo-oxazolidin-3-yl]-2-fluoro-phenylethynyl}-4-hydroxy-piperidine-1-carboxylic acid tert-butyl ester (example 19) (0.95 g, 2 mmol, 1 eq) in methanol/ethyl acetate (20 ml 1/1). The mixture was then hydrogenated using a balloon of hydrogen. When the reaction went to completion, the 10% Pd/C was then removed by filtration over celite and the solid then washed with methanol/ethyl acetate (2×10 ml 1/1). The filtrate and washings were evaporated down to give a white solid (0.96 g, quantitative) that was found pure enough to be carried on without further purification.

General Procedure for the Removal of the T-Butyl Protecting Groups

Hydrogen chloride (1.25 M solution in methanol, 4.0 eq) was added to the amine (1 eq) at room temperature. The mixture is either stirred at room temperature or heated at 40° C. until finished, cooled and then the pH was adjusted to pH10 using saturated sodium hydrogen carbonate solution. The resulting mixture was evaporated and dissolved again with dichloromethane/methanol 9/1. The flask containing the mixture was then placed in an ultrasound bath, sonicated for 5 mins and then filtered. The filtrate was then evaporated to give the product that was then used without further purification, to couple to the quinolone moieties.

Example 24

7-(4-{4-[5S-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-quinoline-3-carboxylic Acid

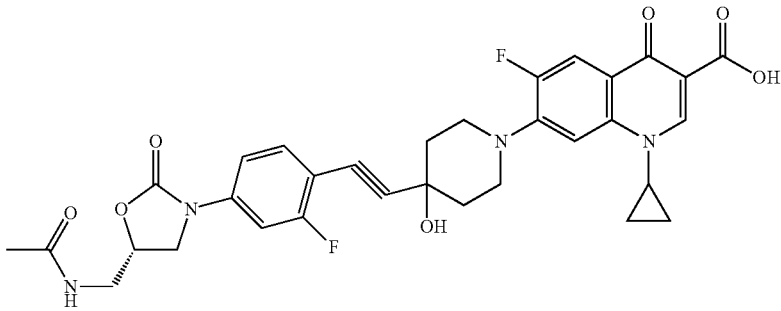 [SMILES: CC(=O)NC[C@H]1CN(c2ccc(C#CC3(O)CCN(c4cc5c(cc4F)c(=O)c(C(=O)O)cn5C4CC4)CC3)c(F)c2)C(=O)O1]

This was prepared by using the general deprotection method for the tert-butyl ester above to give the amine. The resulting amine was then coupled to the required quinoline using the method described in example 5. This gave the required product in 8% yield over two steps.

Example 25

7-(4-{4-[5S-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-[1,8]-napthyridine-3-carboxylic Acid

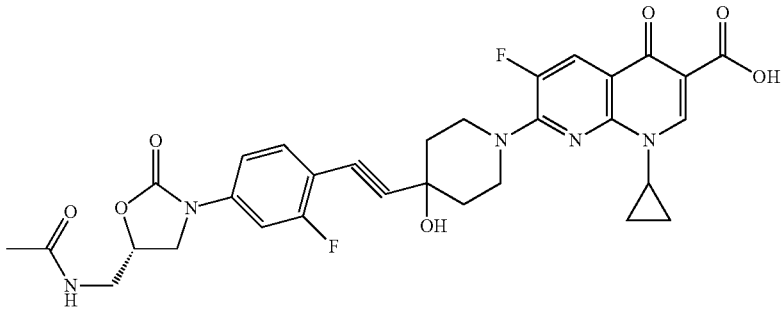 [SMILES: CC(=O)NC[C@H]1CN(c2ccc(C#CC3(O)CCN(c4nc5c(cc4F)c(=O)c(C(=O)O)cn5C4CC4)CC3)c(F)c2)C(=O)O1]

This was prepared by using the general deprotection method for the tert-butyl ester above to give the amine. The resulting amine was then coupled to the required quinoline using the method described in example 1—step 7. This gave the required product in 15% yield over two steps.

Example 26

7-[4-(3-{4-[5S-(acetylamino-methyl)-2-oxo-oxazolidin-3-yl]-2-fluoro-phenyl}-acryloyl)-piperazin-1-yl]-1-cyclopropyl-6-fluoro-4-oxo-1,4-dihydro-quinoline-3-carboxylic Acid

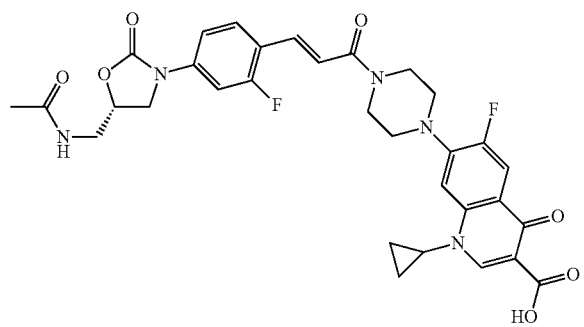 [SMILES: CC(=O)NC[C@H]1CN(c2ccc(/C=C/C(=O)N3CCN(c4cc5c(cc4F)c(=O)c(C(=O)O)cn5C4CC4)CC3)c(F)c2)C(=O)O1]

This was prepared by using the general deprotection method for the tert-butyl ester above to give the amine. The resulting amine was then coupled to the required quinoline using the method described in example 5. This gave the required product in 15% yield over two steps.

Example 27

7-[4-(3-{4-[5S-(acetylamino-methyl)-2-oxo-oxazolidin-3-yl]-2-fluoro-phenyl}-acryloyl)-piperazin-1-yl]-1-cyclopropyl-6-fluoro-4-oxo-1,4-dihydro-[1,8]-napthyridine-3-carboxylic Acid

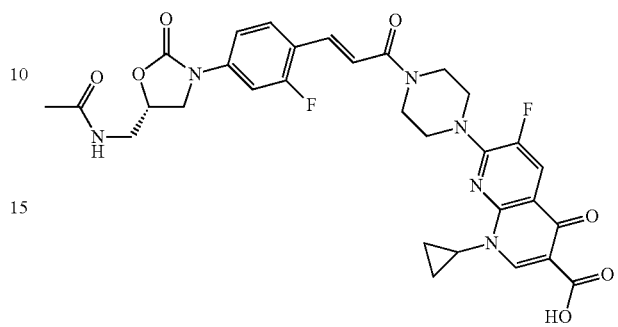

This was prepared by using the general deprotection method for the tert-butyl ester above to give the amine. The resulting amine was then coupled to the required quinoline using the method described in example 1—step 7. This gave the required product in 11% yield over two steps.

Example 28

7-[4-(3-{4-[5S-(acetylamino-methyl)-2-oxo-oxazolidin-3-yl]-2-fluoro-phenoxy}-2-hydroxy-propionyl)-1-cyclopropyl-6-fluoro-4-oxo-1,4-dihydro-quinoline-3-carboxylic Acid

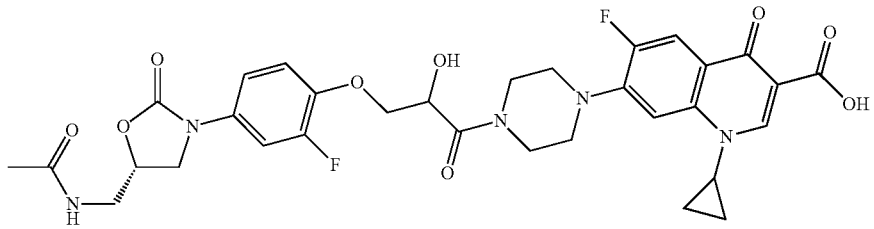 [SMILES: CC(=O)NC[C@H]1CN(c2ccc(OCC(O)C(=O)N3CCN(c4cc5c(cc4F)c(=O)c(C(=O)O)cn5C4CC4)CC3)c(F)c2)C(=O)O1]

This was prepared by using the general deprotection method for the tert-butyl ester above to give the amine. The resulting amine was then coupled to the required quinoline using the method described in example 5. This gave the required product in 5% yield over two steps.

Example 29

7-[4-(3-{4-[5S-(acetylamino-methyl)-2-oxo-oxazolidin-3-yl]-2-fluoro-phenoxy}-2-hydroxy-propionyl)-1-cyclopropyl-6-fluoro-4-oxo-1,4-dihydro-[1,8]-napthyridine-3-carboxylic Acid

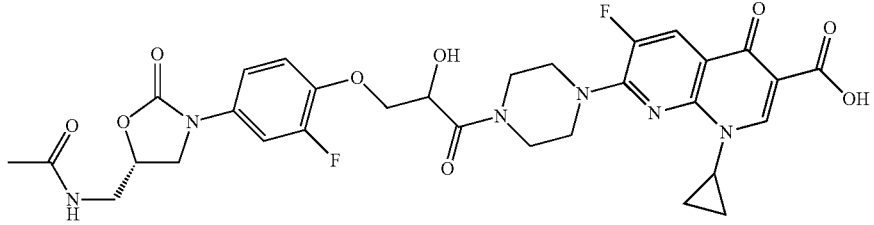 [SMILES: CC(=O)NC[C@H]1CN(c2ccc(OCC(O)C(=O)N3CCN(c4nc5c(cc4F)c(=O)c(C(=O)O)cn5C4CC4)CC3)c(F)c2)C(=O)O1]

This was prepared by using the general deprotection method for the tert-butyl ester above to give the amine. The resulting amine was then coupled to the required quinoline using the method described in example 1—step 7. This gave the required product in 4% yield over two steps.

Example 30

7-[4-(2-{4-[5S-(acetylamino-methyl)-2-oxo-oxazolidin-3-yl]-2-fluoro-phenoxy}-acetyl)-piperazin-1-yl]-1-cyclopropyl-6-fluoro-4-oxo-1,4-dihydro-quinoline-3-carboxylic Acid

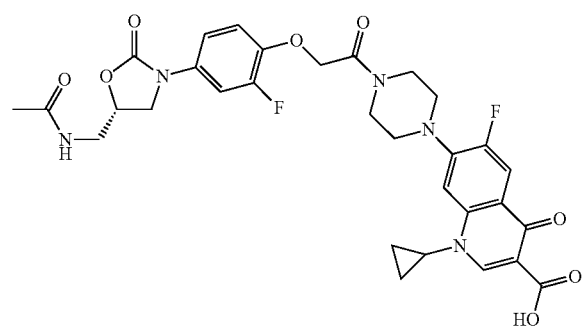 [SMILES: CC(=O)NC[C@H]1CN(c2ccc(OCC(=O)N3CCN(c4cc5c(cc4F)c(=O)c(C(=O)O)cn5C4CC4)CC3)c(F)c2)C(=O)O1]

This was prepared by using the general deprotection method for the tert-butyl ester above to give the amine. The resulting amine was then coupled to the required quinoline using the method described in example 5. This gave the required product in 20% yield over two steps.

Example 31

7-[4-(2-{4-[5S-(acetylamino-methyl)-2-oxo-oxazolidin-3-yl]-2-fluoro-phenoxy}-acetyl)-piperazin-1-yl]-1-cyclopropyl-6-fluoro-4-oxo-1,4-dihydro-[1,8]-napthyridine-3-carboxylic Acid

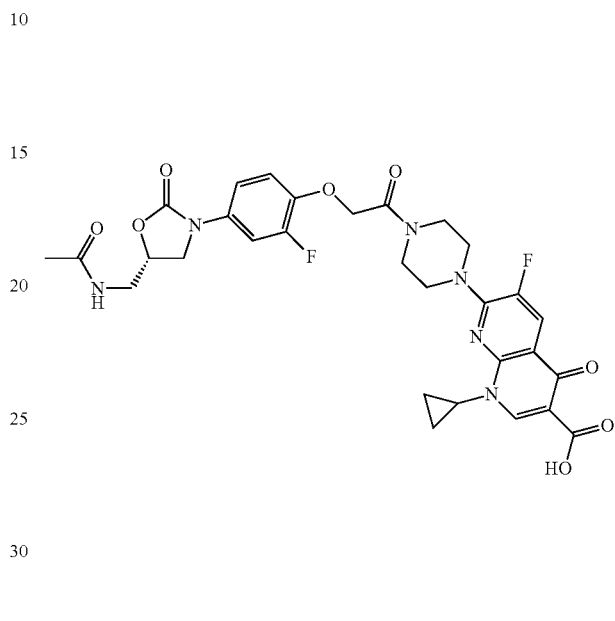

This was prepared by using the general deprotection method for the tert-butyl ester above to give the amine. The resulting amine was then coupled to the required quinoline using the method described in example 1—step 7. This gave the required product in 18% yield over two steps.

Example 32

7-[4-(2-{4-[5S-(acetylamino-methyl)-2-oxo-oxazolidin-3-yl]-2-fluoro-phenyl}-ethyl)-4-hydroxy-piperidin-1-yl]-1-cyclopropyl-6-fluoro-4-oxo-1,4-dihydro-quinoline-3-carboxylic Acid

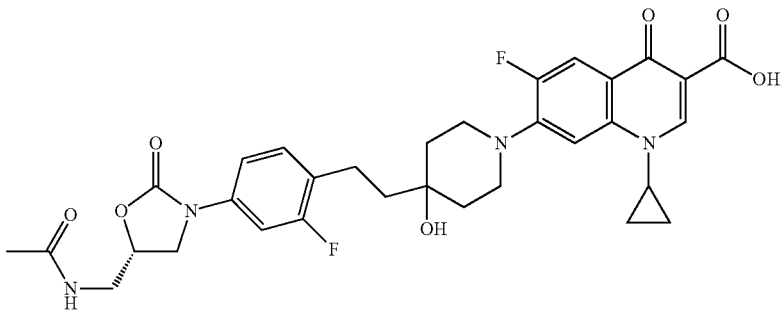 [SMILES: CC(=O)NC[C@H]1CN(c2ccc(CCC3(O)CCN(c4cc5c(cc4F)c(=O)c(C(=O)O)cn5C4CC4)CC3)c(F)c2)C(=O)O1]

This was prepared by using the general deprotection method for the tert-butyl ester above to give the amine. The resulting amine was then coupled to the required quinoline using the method described in example 5. This gave the required product in 10% yield over two steps.

The invention claimed is:

1. A compound of formula (I)

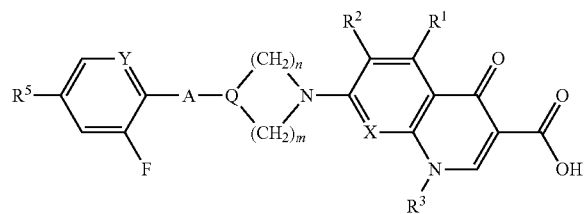

wherein

A is —$CH_2CH_2$—, —$OCH_2$—, or —C≡C—;

Q is $CR^4$;

X is $CR^7$ or N;

Y is CH;

n is 2;

m is 2;

$R^1$ is H;

$R^2$ is H or F;

$R^3$ is an ethyl, a 2-propyl, a $C_3$-$C_6$ cycloalkyl, a phenyl, or a pyridyl group; all of which are optionally substituted with one or more fluorine atoms or amino groups;

$R^4$ is hydroxy, $OSO_3H$, $OPO_3H_2$, $OCH_2OPO_3H_2$, $OCOCH_2CH_2COOH$, or an ester of a naturally occurring amino acid or a derivative thereof, $R^5$ is:

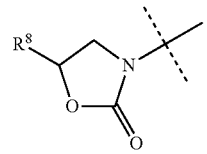

$R^7$ is H or a methoxy group, or $R^3$ and $R^7$ together form a —O—$CH_2$—N(Me)- or —O—$CH_2$—CH(Me)- bridge; and $R^8$ is a $C_{1-6}$ heteroalkyl group;

or a pharmacologically acceptable salt, or formulation thereof.

2. A compound according to claim 1, wherein $R^3$ is a cyclopropyl group.

3. A compound of claim 1, wherein $R^7$ and $R^3$ together form a bridge of the formula —O—$CH_2$—N(Me)- or —O—$CH_2$—CH(Me)-, wherein the stereochemistry at the chiral center is the one giving the (S) configuration in the final compound.

4. A compound of claim 1, wherein X is N or CH.

5. A compound of claim 1, wherein $R^8$ is —$CH_2$NHCOMe.

6. A compound of claim 1, wherein $R^5$ is:

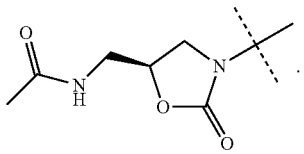

7. A mono, di or tri sodium salt of a compound of formula (I) according to claim 1.

8. A compound of claim 7 wherein $R^4$ is $OPO_3H_2$ or $OSO_3H$ or mixtures thereof.

9. A pharmaceutical composition comprising a compound of claim 1.

10. The pharmaceutical composition of claim 9 further comprising one or more optionally carriers and/or adjuvants and/or diluents.

* * * * *